US009404872B1

(12) United States Patent
Wang et al.

(10) Patent No.: US 9,404,872 B1
(45) Date of Patent: Aug. 2, 2016

(54) SELECTABLY CONFIGURABLE MULTIPLE MODE SPECTROSCOPIC ELLIPSOMETRY

(75) Inventors: Haiming Wang, Fremont, CA (US); Guorong V. Zhuang, Santa Clara, CA (US); Shankar Krishnan, Santa Clara, CA (US); Klaus Flock, Mountainview, CA (US); Johannes D. de Veer, Menlo Park, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 780 days.

(21) Appl. No.: 13/538,552

(22) Filed: Jun. 29, 2012

Related U.S. Application Data

(60) Provisional application No. 61/502,507, filed on Jun. 29, 2011, provisional application No. 61/527,884, filed on Aug. 26, 2011.

(51) Int. Cl.
*G01J 4/00* (2006.01)
*G01N 21/55* (2014.01)
*G01N 21/88* (2006.01)
*G01N 21/21* (2006.01)

(52) U.S. Cl.
CPC .......... *G01N 21/8806* (2013.01); *G01N 21/211* (2013.01)

(58) Field of Classification Search
CPC ............ G01N 21/8806; G01N 21/211; G01N 21/95607; G01N 21/4788; G01N 2021/213; G01B 2210/56; G01B 11/0625; G01B 11/24; G01B 11/02; G01B 11/0641
USPC ................................................. 356/369, 447
See application file for complete search history.

(56) References Cited

U.S. PATENT DOCUMENTS

| 5,333,052 A * | 7/1994 | Finarov .............. G01B 11/0641 356/369 |
| 5,450,201 A * | 9/1995 | Katzir et al. ................... 356/369 |
| 5,581,350 A | 12/1996 | Chen et al. |
| 5,608,526 A | 3/1997 | Piwonka-Corle et al. |
| 5,798,837 A | 8/1998 | Aspnes et al. |
| 6,734,968 B1 | 5/2004 | Wang et al. |
| 2003/0147076 A1* | 8/2003 | Bowman ........................ 356/369 |
| 2007/0181794 A1* | 8/2007 | Walsh et al. ................ 250/252.1 |

(Continued)

OTHER PUBLICATIONS

P.S. Hauge, "Mueller Matrix Ellipsometry with Imperfect Compensators", JOSA A 68(11), 1519-1528, 1978.
R.M.A. Azzam, "A Simple Fourier Photopolarimeter with Rotating Polarizer and Analyzer for Measuring Jones and Mueller Matrices", Opt Comm 25(2), 137-140, 1978.

(Continued)

*Primary Examiner* — Tarifur Chowdhury
*Assistant Examiner* — Sunghee Y Gray
(74) *Attorney, Agent, or Firm* — Suiter Swantz pc llo

(57) ABSTRACT

The present invention may include an illumination source configured to illuminate a surface of a sample, a detector configured to detect at least a portion of light reflected from the surface of the sample, a selectably configurable optical system comprising: a rotatable polarizing element disposed in the illumination arm of the optical system, an analyzing element disposed in the collection arm of the optical system, and a rotatable-translatable compensator element disposed in the collection arm of the optical system, and a control system communicatively configured to selectably configure the optical system in the a rotating compensator (RCSE) mode, a rotating polarizer (RPSE) mode, or a rotating polarizer and compensator (RPRC) mode.

30 Claims, 13 Drawing Sheets

(56) References Cited

U.S. PATENT DOCUMENTS

| | | | |
|---|---|---|---|
| 2009/0279090 A1* | 11/2009 | Wolf et al. ................... | 356/369 |
| 2012/0057158 A1* | 3/2012 | Hilfiker ............... | G01N 21/211 |
| | | | 356/369 |
| 2012/0257200 A1* | 10/2012 | Blasenheim ............. | G02B 7/28 |
| | | | 356/369 |
| 2012/0268740 A1* | 10/2012 | Walsh et al. ................. | 356/327 |
| 2015/0168290 A1* | 6/2015 | Shachaf ................... | G02B 7/28 |
| | | | 356/369 |

OTHER PUBLICATIONS

M.L. Aleksandrov, et al., "Methods and Apparatus for Complete Ellipsometry (Review)", J Appl Spectroscopy 44(6), 559-578, 1986.
Hamamatsu, Xenon Lamps, Electron Tube Division, Product Page found online at: https://web.archive.org/web/20100406012714/http://sales.hamamatsu.com/en/products/electron-tube-division/light-sources/xenon-lamps.php, printed Feb. 4, 2015.

* cited by examiner

214

216
218 SUBSTRATE 220
228
222  224
226

SUBSTRATE

SELECTABLY CONFIGURABLE MULTIPLE MODE SPECTROSCOPIC ELLIPSOMETRY

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of U.S. Provisional Patent Application entitled APPARATUS AND METHODS OF LIGHT SOURCE TRACKING IN OPTICAL METROLOGY MEASUREMENT SYSTEM, naming Shankar Krishnan, Guorong Vera Zhuang, Klaus Flock, and Johannes D. de Veer, as inventors, filed Jun. 29, 2011, Application Ser. No. 61/502,507.

For purposes of the USPTO extra-statutory requirements, the present application constitutes a regular (non-provisional) patent application of U.S. Provisional Patent Application entitled SYSTEMS AND METHODS FOR CONDUCTING MULTIPLE SPECTROSCOPIC ELLIPSOMETRIC MEASUREMENTS IN SEMICONDUCTOR MANUFACTURING PROCESSES, naming Shankar Krishnan and Haiming Wang, as inventors, filed Aug. 26, 2011, Application Ser. No. 61/527,884.

TECHNICAL FIELD

The present invention generally relates to a method and system for performing spectroscopic ellipsometry, and, in particular, a method and system for performing multiple mode spectroscopic ellipsometry.

BACKGROUND

Broadband spectrum illumination sources are commonly implemented in spectroscopic based optical metrology tools. Such broadband based metrology tools may be utilized to measure various parameters associated with a given sample, such as a semiconductor wafer or lot of semiconductor wafers. Fabricating semiconductor devices such as logic and memory devices typically includes processing a substrate such as a semiconductor wafer using a large number of semiconductor fabrication processes to form various features and multiple levels of the semiconductor devices.

One type of broadband based metrology includes spectroscopic ellipsometry (SE). Spectroscopic ellipsometry (SE) is commonly implemented in order to measure thicknesses of film stacks on semiconductor wafers and critical dimensions (CD) of semiconductor structures in a variety of semiconductor manufacturing processes. One type of SE system includes a rotating polarizer SE (RPSE), which typically includes a broadband light source (e.g., xenon lamp), a rotating polarizer, a fixed analyzer (may be rotated at discrete angles), and a spectroscopic detector. RPSE is an extremely powerful tool, initially used for film thickness measurements, and is now widely applied to measure both film thicknesses and critical dimensions of samples. Another type of SE system includes the rotating compensator spectroscopic ellipsometer (RCSE), which typically includes a broadband light source, a fixed polarizer, a rotating waveplate (i.e., "compensator" in ellipsometry), a fixed analyzer, and a spectroscopic detector.

As critical dimensions (e.g., the gate width or gate oxide thickness) continue to decrease, measurement of these ever shrinking dimensions (e.g., a few nanometers or sub-nanometer) requires improved measurement performance. One of the fundamental performance requirements includes measurement precision, or the so called "3-sigma" of the measured CD parameters. An additional challenge includes tool-to-tool matching. Both requirements are related to the sensitivity of the implemented measurement system. As the system parameters decrease, the measurable signal change, corresponding to the fractional change in given parameters, are often not distinguishable from system noise for commonly implemented standard RPSE and RCSE systems. As a result, prior art implementations are insufficient both in terms of precision and tool-to-tool matching capability.

One method to improve measurement sensitivity includes the measurement of an increased number of spectral properties associated with geometric and material structures of a given sample. In an RPSE system, a motor is used to drive a polarizer with angular frequency $\omega$. The signal measured by the detector of the system consists of three harmonic terms, known as the DC term, and terms related to $\cos 2\omega t$ and $\sin 2\omega t$, respectively. In practice, the DC term is used to normalize the $\cos 2\omega t$ and $\sin 2\omega t$ harmonics, resulting in the commonly termed [$\alpha$, $\beta$] spectra. As a result, one can measure two sets of combinations of Mueller elements, normalized by the first Mueller element ($M_{00}$). Similarly, in an RCSE system, one may obtain three normalized harmonics, and is then able to measure three combinations of Mueller elements normalized by the first Mueller element ($M_{00}$).

A common approach to measuring additional Mueller elements includes Mueller SE, also referred to as "complete SE," which includes the implementation of two rotating polarizing elements. One such complete SE system includes a dual-rotating compensator SE (DRCSE) system, which includes a light source, a fixed polarizer, a first rotating waveplate in the illumination path, a second rotating waveplate in the collection path, a fixed analyzer, and a detector. This complete SE system configuration is capable of collecting up to 25 harmonic coefficients, corresponding to certain linear combinations of the rotation frequencies of these two rotating compensators. As a result, all 15 normalized Mueller elements can be resolved and measured.

Enhanced sensitivity of Mueller SE is advantageous for measuring small CD parameter changes. Nevertheless, this enhanced sensitivity will also cause the given measurement system to be more susceptible to system errors, due to the sensitivity of the additional Mueller elements to perturbations in the system. As a result, improved systems and methods for calibration of critical ellipsometry parameters are desirable.

SUMMARY

An apparatus suitable for multiple mode spectroscopic ellipsometry is disclosed. In one aspect, an apparatus may include, but is not limited to, an illumination source configured to illuminate a surface of a sample disposed on a sample stage; a detector configured to detect at least a portion of light reflected from the surface of the sample; a selectably configurable optical system including an illumination arm and a collection arm, the illumination source and the detector being optically coupled by the optical system, the optical system further comprising: a rotatable polarizing element disposed in the illumination arm of the optical system, the rotatable polarizing element being rotatable about an optical axis of the illumination arm; an analyzing element disposed in the collection arm of the optical system and arranged at a selected analyzer angle; and a rotatable-translatable compensator element disposed in the collection arm of the optical system, the rotatable-translatable compensator element being rotatable about an optical axis of the collection arm, the rotatable-translatable compensator element being linearly translatable along a direction perpendicular to the optical axis of the collection arm; and a control system communicatively coupled to the rotatable polarizing element and the rotatable-translatable compensator element, wherein the control system is configured to selectably configure the optical system in at least one of a rotating compensator (RCSE) mode, a rotating polarizer (RPSE) mode, and a rotating polarizer and compensator (RPRC) mode by controlling an operation state of at least one of the rotatable polarizing element and the rotatable-translatable compensator element.

In a further embodiment, the apparatus may include a multi-axis actuation control system, wherein the illumination source is disposed on a multi-axis actuation stage of the multi-axis actuation control system; an additional control system communicatively coupled to the multi-axis actuation control system and the detector, wherein the control system is configured to: acquire a set of diagnostic parameters from a diagnostic sample disposed on the sample stage, wherein the set of diagnostic parameters are indicative of position drift of the illumination source as measured relative to one or more components of the optical system; determine a magnitude of illumination source position drift by comparing the acquired set of diagnostic parameters to an initial set of parameters obtained from the diagnostic sample at a previously measured alignment condition; determine a direction of illumination source position drift; and provide a set of illumination source position adjustment parameters configured to correct the determined magnitude and direction of the illumination source position drift to the multi-axis actuation control system.

An apparatus suitable for calibration of one or more ellipsometric parameters is disclosed. In one aspect, an apparatus may include, but is not limited to, an illumination source configured to illuminate a surface of a calibration sample disposed on a sample stage; a detector configured to collect at least a portion of light reflected from the surface of the calibration sample; a selectably configurable optical system including an illumination arm and a collection arm, the illumination source and the detector being optically coupled by the optical system, the optical system further comprising: a rotatable polarizing element disposed in the illumination arm of the optical system, the rotatable polarizing element being rotatable about an optical axis of the illumination arm; an analyzing element disposed in the collection arm of the optical system and arranged at a selected analyzer angle; and a rotatable-translatable compensator element disposed in the collection arm of the optical system, the rotatable-translatable compensator element being rotatable about an optical axis of the collection arm, the rotatable-translatable compensator element being linearly translatable along a direction perpendicular to the optical axis of the collection arm; and a control system communicatively coupled to the rotatable polarizing element and the rotatable and translatable compensator element, wherein the control system is configured to: configure the optical system in at least one of a rotating compensator (RCSE) mode, a rotating polarizer (RPSE) mode, and a rotating polarizer and compensator (RPRC) mode; measuring one or more spectroscopic ellipsometry properties of one or more calibration samples in at least one of the RCSE mode, the RPSE mode, and the RPRC mode; and calibrating one or more parameters of the optical system utilizing the measured one or more spectroscopic ellipsometry properties.

A method for performing multiple mode spectroscopic ellipsometry is disclosed. In one aspect, a method may include, but is not limited to, selectably configuring an optical system of the spectroscopic ellipsometer in at least one of a rotating compensator (RCSE) mode, a rotating polarizer (RPSE) mode, and a rotating polarizer and compensator (RPRC) mode; illuminating a surface of a sample disposed on a sample stage via an illumination arm of the optical system; and detecting at least a portion of light reflected from the surface of the sample via a collection arm of the optical system.

In a further embodiment, the method includes measuring one or more spectroscopic ellipsometry properties of one or more calibration samples in at least one of the RCSE mode, the RPSE mode, and the RPRC mode; and calibrating the optical system utilizing the measured one or more spectroscopic ellipsometry properties.

In another aspect, a method may include, but is not limited to, selectably configuring an optical system of the spectroscopic ellipsometer in at least one of a rotating compensator (RCSE) mode, a rotating polarizer (RPSE) mode, and a rotating polarizer and compensator (RPRC) mode; illuminating a surface of a diagnostic sample disposed on a sample stage via an illumination arm of the optical system utilizing an illumination source disposed on a multi-axis actuation stage of a multi-axis actuation control system; detecting at least a portion of light reflected from the surface of the diagnostic sample via a collection arm of the optical system, wherein the illumination source and the detector are optically direct-coupled via the optical system; acquiring a set of diagnostic parameters indicative of illumination source position drift from the diagnostic sample; determining a magnitude of the illumination source position drift by comparing the acquired set of diagnostic parameters to an initial set of parameters obtained from the diagnostic sample at a previously measured alignment condition; determining a direction of the illumination source position drift; and providing a set of illumination source position adjustment parameters configured to correct the determined magnitude and direction of the illumination source position drift to the multi-axis actuation control system of the multi-axis sample stage.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A through 5, systems for performing multimode spectroscopic ellipsometry are described in accordance with the present disclosure. The present disclosure is directed toward systems and methods for performing multimode spectroscopic ellipsometry on a single platform, allowing for the selectable configuration of the system in one of multiple spectroscopic ellipsometry modes. In this regard, the system may be configured in one of a rotating polarizer SE (RPSE) mode, a rotating compensator SE (RCSE), or a rotating polarizer-rotating compensator SE (RPRC SE) mode. The present disclosure is also directed to a systematic, self-consistent, and unified calibration methodology, allowing for calibration of the multimode system across all modes. The unique ability of the system to be configured in multiple modes provides enhanced calibration ability, which in turn provides enhanced measurement sensitivity and accuracy. The improved sensitivity and calibrated systematic error provided by the present invention in turn provides for improved tool-to-tool matching. The present disclosure is further directed to the implementation of multimode spectroscopic ellipsometry (MMSE) in a direct coupled optical setting with illumination source tracking and feedback, which may further improve the stability and sensitivity of the presently disclosed selectably configurable MMSE system.

Figure 1A:
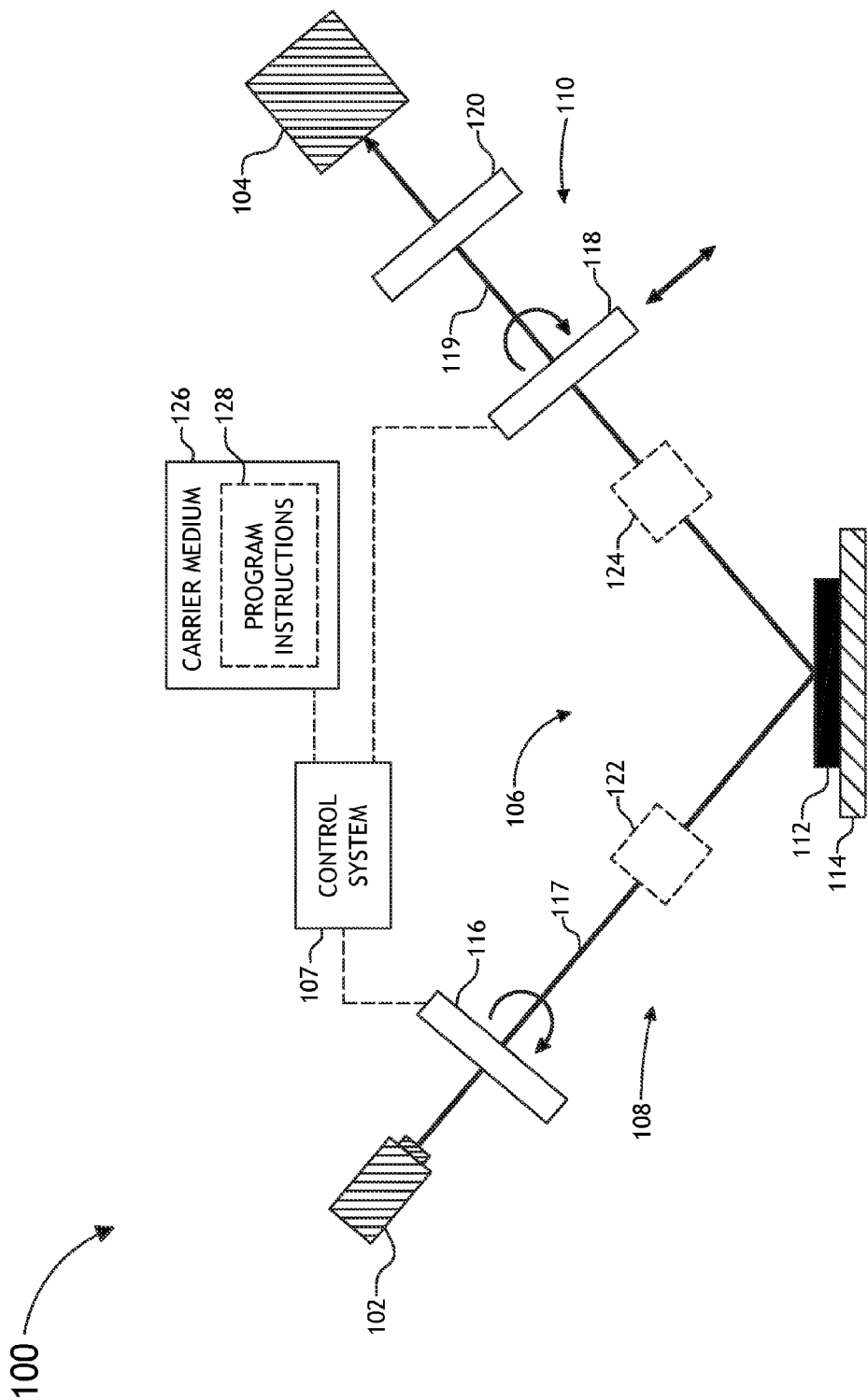
FIG. 1A illustrates a schematic view of a selectably configurable multimode spectroscopic ellipsometry (MMSE) system, in accordance with one embodiment of the present invention.

FIG. 1A illustrates a schematic view of a configurable multiple mode spectroscopic ellipsometer 100, in accordance with one embodiment of the present invention. The system 100 may include an illumination source 102 configured to illuminate a surface of a sample 112 disposed on a sample stage 114, a detector 104 configured to detect light reflected from the surface of the sample 112, and a selectably configurable optical system 106, which acts to optically couple the illumination source 102 and the detector 104. The system 100 may further include a computer control system 107 suitable for controlling the configuration of the selectably configurable optical system 106.

In one aspect of the present invention, the selectably configurable optical system 106 of the system 100 may include an illumination arm 108 and a collection arm 110. The illumination source 102 and the detector 104 may be optically coupled via the illumination arm 108 and the collection arm 110 of the optical system 106. In this manner, light may emanate from the illumination source 102 and travel along the illumination arm 108 to the surface of the sample 112. Light reflected from the sample 112 may then travel from the surface of the sample 112 to the detector 104 along the collection arm 110.

In another aspect of the present invention, the illumination arm 108 of the optical system 106 may include a rotatable polarizing element 116. In one aspect, the rotatable polarizing element 116 is configured for selective rotation about the optical axis of the illumination pathway 117 of the illumination arm 108 of the optical system 106. In a general sense, the rotatable polarizing element 116 may include any polarizer and means for rotating the polarizer known in the art. For example, the rotatable polarizing element 116 may include a polarizer mechanically coupled to a rotatable motor. It is recognized herein that the polarizer of the rotating polarizing element 116 may include any polarizer known in the art. For example, the polarizer may include a rotating polarizer, such as but not limited to, a Rochon prism. In another example, the polarizer may include a beam displacer. The rotatable polarizer element 116 is configured to operate within the system 100 in either a rotationally active or rotationally inactive state. For instance, a rotatable motor of the rotatable polarizing element 116 may be inactive such that the rotating element 116 remains rotationally fixed about the axis 117 of the illumination arm 108. In another instance, the rotatable motor may act to rotate the polarizer of a rotatable polarizing element 116 at a selected angular frequency, $\omega_p$, about the optical axis 117 of the illumination arm 108.

In another aspect of the present invention, the collection arm 110 of the optical system 106 may include a rotatable-translatable compensator element 118. In one aspect, the rotatable-translatable compensator element 118 is configured for selective rotation about the optical axis of the optical pathway 119 of the collection arm 110 of the optical system 106. In addition, the rotatable-translatable compensator element 118 is configured for the selective translation in and out of the optical pathway 119 of the collection arm 110. In a general sense, the rotatable-translatable compensator element 118 may include any compensator (e.g., waveplate) and means for rotating and/or translating the compensator known in the art. For example, the rotatable-translatable compensator element 118 may include a compensator mechanically coupled to a rotatable motor, wherein the rotatable motor is further coupled to a linear translation stage suited for moving the compensator-rotational motor assembly in and out of the collection pathway 119. It is recognized herein that the compensator of the rotatable-translatable compensator element 118 may include any compensator known in the art suitable for ellipsometry analysis. The rotatable-translatable compensator element 118 is configured to operate within the system 100 in either a rotationally active or rotationally inactive state. For instance, the translation stage coupled to the compensator may be controlled to either place the compensator element 118 within the collection pathway 119 or remove the element 118 from the pathway 119. Further, the rotatable-translatable compensator element 118 is configured to operate within the system 100 in either a rotationally active or rotationally inactive state. For instance, a rotatable motor of the rotatable-translatable compensator element 118 may be inactive such that the element 118 remains rotationally fixed about the axis 119 of the collection arm 110. In another instance, the rotatable motor may act to rotate the compensator of the rotatable-translatable compensator element 118 at a selected angular frequency, $\omega_c$, about the optical axis 119 of the collection arm 110.

In another aspect of the invention, the collection arm 110 of the optical system 106 may include an analyzer 120. In one embodiment, the analyzer 120 may be arranged at a fixed analyzer angle. For example, the analyzer 120 may be arranged at a fixed analyzer angle of −25°.

In a general sense, the system 100 may provide for multiple configurations of the various polarizing elements of the system (i.e., polarizing element 116, compensator element 118, or analyzer 120). In this regard, the system 100 may provide for any combination of a rotational condition of the polarizing element 116, compensator element 118, or analyzer 120. For example, the polarizer, compensator and analyzer of the system 100 may each rotate continuously or discretely. Further, the polarizer, compensator, and analyzer may rotate simultaneously or in any combination with one another. For instance, the polarizer and compensator may rotate simultaneously in a continuous or discrete fashion. In another, instance the polarizer and analyzer may rotate simultaneously in a continuous or discrete fashion. Even further, the analyzer and compensator may rotate simultaneously in a continuous or discrete fashion. The system 100 of the present invention provides for complete control of all rotational conditions of the various polarizing elements of the optical system 106 in a single platform environment.

In another aspect of the invention, the control system 107 may configure the multimode system 100 into one of multiple modes. For example, the control system 107 may control the rotatable polarizing element 116 and/or the rotatable-translatable compensator element 118 in order to configure the system 100 into one of the RPSE mode, the rotating compensator spectroscopic ellipsometry RCSE mode, or the RPRC SE mode. In this regard, the control system 107 may consist of a computing system configured to control the rotatable polarizing element 116 and/or the rotatable-translatable compensator element 118 in order to achieve one of the above selected modes (discussed in greater detail further herein).

It should be recognized that the various control steps associated with configuring of the multimode system 100 described throughout the present disclosure may be carried out by a single computer system 107 or, alternatively, a multiple computer system 107. Moreover, different subsystems of the system 100 may include a computer system suitable for carrying out at least a portion of the steps described above. Further, the one or more computer systems 107 may be configured to perform any other step(s) of any of the method embodiments described herein.

In another embodiment, the computer control system 107 may be communicatively coupled to the rotatable polarizing element 116, the rotatable-translatable compensator element 118, the illumination source 102 or detector 104 in any manner known in the art. For example, the computer control system 107 may be communicatively coupled to the various sub-systems of system 100 via a wireline or wireless connection.

The computer control system 107 may include, but is not limited to, a personal computer system, mainframe computer system, workstation, image computer, parallel processor, or any other device known in the art. In general, the term "computer system," "computing system(s)," or "computer control system" may be broadly defined to encompass any device(s) having one or more processors, which execute instructions from a memory medium.

Program instructions 128 implementing methods such as those described herein may be transmitted over or stored on carrier medium 126. The carrier medium 126 may be a transmission medium such as a wire, cable, or wireless transmission link. The carrier medium 126 may also include a storage medium such as a read-only memory, a random access memory, a magnetic or optical disk, or a magnetic tape.

In one embodiment, the computer control system 107 may receive user inputted instructions via a user interface (not shown). In response to user inputted instructions, the control system 107 may act to configure the multimode system 100 into one of the RPSE mode, the RCSE mode, or the RPCE SE mode. For example, the control system 107 may display a set of mode selections to a user via a display (not shown). The user may then select one or more of the selections via a user interface device (not shown). In response to this selection, the control system 107 may transmit control signals to the rotatable polarizing element 116 and/or the rotatable-translatable compensator element 118 in order to direct the elements 116 or 118 to adjust in order to correspond with the selected configuration.

In another embodiment, the system 100 need not require a centralized control system. In this sense, the rotatable polarizing element 116 and the rotatable-translatable compensator element 118 of the system 100 may be controlled by independent controllers each configured to receive user input independently.

In additional embodiments, the illumination arm 108 and/or the collection arm 110 may include, but are not limited to, one or more additional optical elements, 122 and 124. Those skilled in the art should recognize that numerous optical elements 122, 124 may be utilized within the illumination arm 108 or collection arm 110 within the scope of the present invention. For example, the optical elements 122 of the illumination arm 108 may include, but are not limited to, one or more lenses (e.g., focusing lenses), one or more mirrors, one or more filters, or one or more collimators. Similarly, the optical elements 124 of the collection arm 110 may include, but are not limited to, one or more lenses, one or more mirrors, one or more filters, or one or more collimators.

In another aspect of the present invention, the Illumination source 102 may include any broadband illumination source known in the art. In one embodiment, the illumination source 102 may include, but is not limited to, a halogen light source (HLS). For instance, the halogen light source may include, but is not limited to, a tungsten based halogen lamp. In another example, the illumination source 102 may include a xenon arc lamp. By yet another example, the illumination source 102 may include a deuterium arc lamp. In a general sense, any illumination source capable of producing illumination in the visible, infrared, and ultraviolet spectral ranges is suitable for implementation in the present invention. For example, a xenon arc lamp is capable of delivering light in a spectral range of 190 nm to 2000 nm, with a gradual radiant intensity decrease below 400 nm. In another embodiment, the illumination source 102 may include, but is not limited to, any discharge plasma source known in the art. In yet another embodiment, the illumination source 102 may include, but is not limited to, a laser-driven plasma source. It should be recognized by those skilled in the art that the above described illumination sources do not represent limitations, but should merely be interpreted as illustrative.

It is noted that the above description relating to the various types of illumination sources should not be interpreted as limiting, but rather merely as illustrative. Those skilled in the art should recognize that any broadband illumination source is suitable for implementation in the present invention. Moreover, it is further contemplated herein that two or more broadband illumination source may be combined in order to tailor to a required broadband spectral range. In this manner, a first source emitting illumination in a first spectral range may be combined with a second source emitting illumination in a second spectral range. For example, a first light source may include a xenon lamp, while a second light source may include a deuterium lamp.

In another aspect of the present invention, the detector 104 may include any light detection system known in the art suitable for implementation in a broadband spectrometer, ellipsometer, reflectometer, or scatterometer setting. In a general sense, any detector capable of measuring spectra across the visible, infrared, and ultraviolet spectral ranges is suitable for implementation in the present invention.

In one embodiment of the present invention, the illumination source 102 of multiple mode SE system 100 may be coupled to the collection optics of the system via one or more optical fibers (not shown). In a fiber-coupled optical setting, the optical fiber of the system 100 may be utilized to present light from a broadband source 102 to the collection optics of the system 100. The utilization of optical fiber to couple a broadband source to collection optics aids in improving pointing stability and intensity fluctuations created due to beam pointing errors. Moreover, optical fiber may act as a light scrambler, causing the intensity spatial distribution of the transmitted light to become more uniform as it propagates through the optical fiber. Further, the spatial dimension of the illumination source (as it is presented to the collection optics) is defined by the physical diameter of the optical fiber. As such, optical fiber plays a key role in both beam shaping and beam stabilization.

In another embodiment of the present invention, the illumination source 102 of the multiple mode SE system 100 may be direct-coupled to the detector 104 of the system 100. While it is contemplated herein that the system 100 is applicable in settings wherein the illumination source 102 and detector 104 are coupled via an optical fiber, due to the degradation of UV throughput in optical fibers as a result of solarization and UV enhanced photocontamination, in certain instances, it is desirable to operate the multimode SE system 100 in a direct-coupled configuration.

As used throughout the present disclosure, the term "direct-coupling" generally refers to a configuration wherein light from an illumination source is delivered to a measurement system (e.g., detector 104) through free space (i.e., no intervening transmission medium, such as an optical fiber). The direct free space coupling may take place in vacuum, an ambient atmosphere, or a purged environment (e.g., inert gas purge). As will be discussed in greater detail further herein, the implementation of a direct-coupled illumination-detector system may lead to instabilities in the position of the illumination source 102 relative to the measurement optics of the system 100. It is generally desirable to maintain the relative position of the illumination source 102 with respect to the measurement optics, allowing for long term measurement system stability.

In another embodiment of the present invention, the selectably configurable optical system 106 may include a reflective-based optical system. In an alternative embodiment, the selectably configurable optical system 106 may include a refractive-based optical system.

Figure 1B:
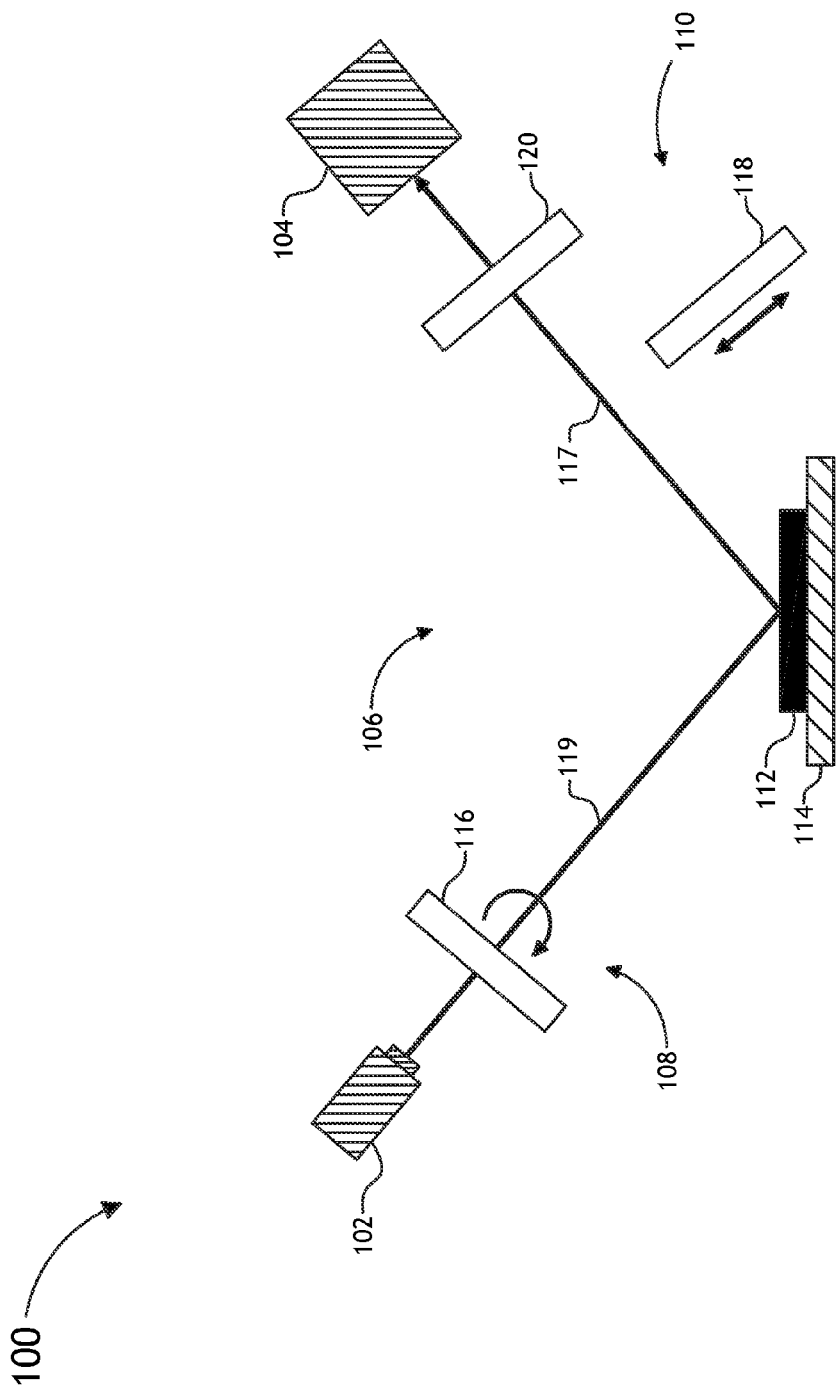
FIG. 1B illustrates a schematic view of a rotating polarizing spectroscopic ellipsometry (RPSE) mode of the selectably configurable MMSE system, in accordance with one embodiment of the present invention.

FIG. 1B illustrates the rotating polarizing spectroscopic mode (RPSE) of the multimode system 100. In the RPSE mode, the compensator is "flipped out" or removed from the collection path 117 of the collection arm 110. In this manner, the linear translation stage of the rotatable-translatable element 118 acts to translate the compensator along a direction generally perpendicular to the collection path 119. While in the RPSE mode, the system 100 may rotate the polarizer of the rotatable polarizer element 116 using a rotation motor at an angular frequency of $\omega_p$. Further, the analyzer 120 is set at a fixed analyzer angle (e.g., 25°). Rotating polarizer based spectroscopic ellipsometry is generally described in U.S. Pat. No. 5,581,350 and U.S. Pat. No. 5,608,526, which are incorporated herein in their entirety.

In the RPSE mode, the detector signal may be expressed in terms of three harmonics of the frequency of the rotating polarizer, $\omega_p$. In this regard, the detector signal is given by:

$$S_D = S_F[f_0 + f_1 \cos 2\omega_p t + f_2 \sin 2\omega_p t] \quad \text{(Eq. 1)}$$

where the scale factor, $S_F$, is proportional to the intensity of the incident light beam, $I_i$, and the fixed analyzer angle, respectively. The scale factor, intensity, and harmonic coefficients $f_0$, $f_1$, and $f_2$ are given by:

$$S_F = \frac{I_i}{4} \quad \text{(Eq. 2)}$$

$$f_0 = M_{00} + M_{10} \cos 2A - M_{20} \sin 2A$$

$$f_1 = M_{01} + M_{11} \cos 2A - M_{21} \sin 2A$$

$$f_2 = -(M_{02} + M_{12} \cos 2A - M_{22} \sin 2A) \quad \text{(Eq. 3)}$$

In this regard, the detector signal $S_D$ consists of three harmonics of the polarizer angle $P = \omega_p t$. These second harmonic coefficients are then normalized to produce the standard [α,β] factors in the RPSE mode, given by:

$$\alpha = \frac{f_1}{f_0} = \frac{M_{01} + M_{11} \cos 2A - M_{21} \sin 2A}{M_{00} + M_{10} \cos 2A - M_{20} \sin 2A} \quad \text{(Eq. 4)}$$

-continued $$\beta = \frac{f_2}{f_0} = -\frac{M_{02} + M_{12}\cos 2A - M_{22}\sin 2A}{M_{00} + M_{10}\cos 2A - M_{20}\sin 2A}$$

Utilizing these factors and their relationship to the associated Mueller matrix components, the RPSE mode of the system 100 may be fully calibrated.

Figure 1C:
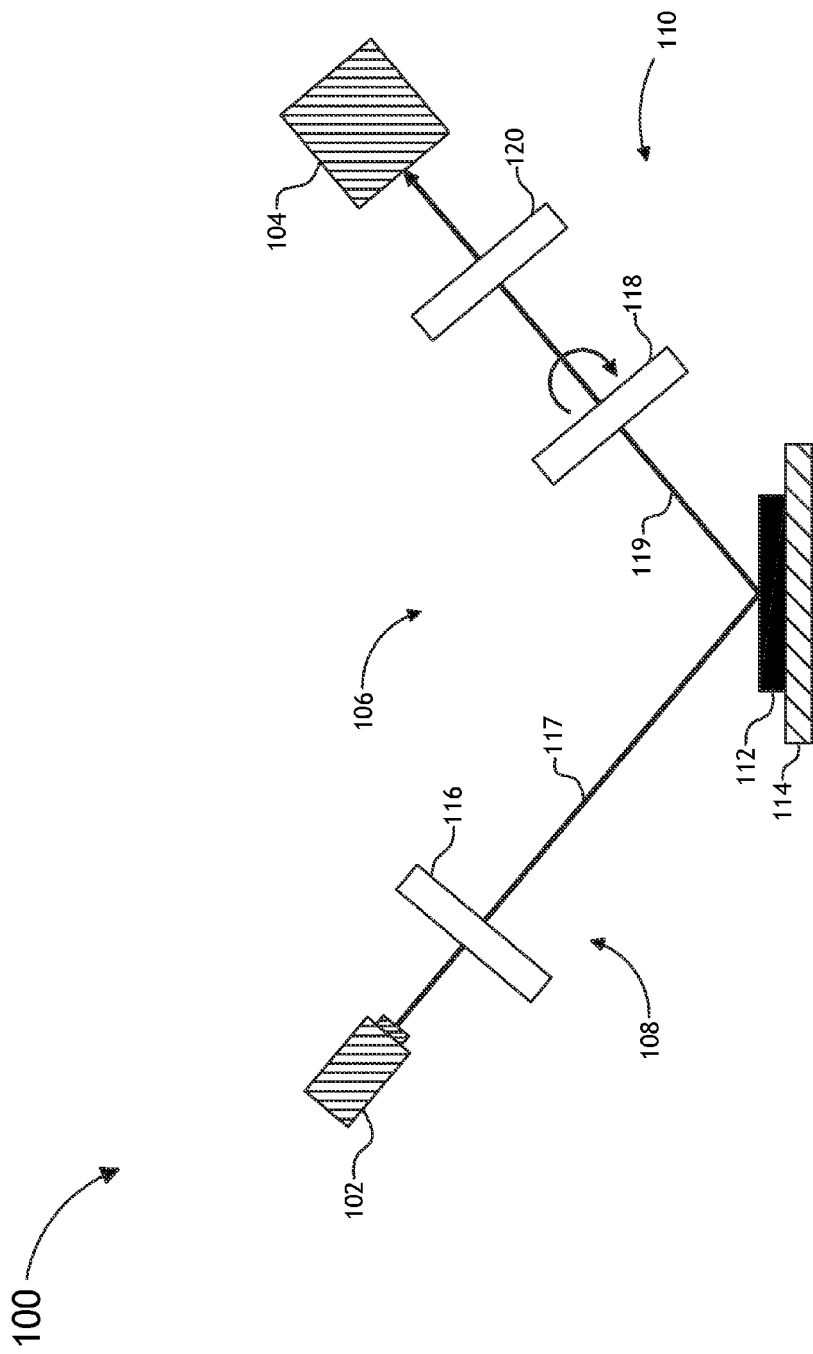
FIG. 1C illustrates a schematic view of a rotating compensator spectroscopic ellipsometry (RCSE) mode of the selectably configurable MMSE system, in accordance with one embodiment of the present invention.

FIG. 1C illustrates the rotating compensator spectroscopic mode (RCSE) of the multimode system 100. In the RCSE mode, the compensator is "flipped in" the collection path 119 of the collection arm 110. In this manner, the linear translation stage of the rotatable-translatable element 118 acts to translate the compensator along a direction generally perpendicular to the collection path 119 until the compensator is positioned adequately in the optical pathway 119 of the collection arm 110. In the RCSE mode, the system 100 rotates the compensator of the rotatable-translatable polarizer element 118 using a rotation motor at an angular frequency of $\omega_c$. Further, the polarizer of the rotatable polarizing element 116 is fixed at a selected polarizer angle, while the analyzer 120 is set at a fixed analyzer angle. Rotating compensator based spectroscopic ellipsometry is generally described in U.S. Pat. No. 5,798,837, which is incorporated herein in its entirety.

In the RCSE mode, the detector signal may be expressed in terms of five harmonics (with only four of them being independent) of the rotating compensator angle, $C=\omega_c t$. In this regard, the detector signal is given by:

$$S_D = S_F[f_0 + f_1 \sin 2(A - \omega_c t) + f_3 \cos 4\omega_p t + f_4 \sin 4\omega_p t] \quad (Eq. 5)$$

where the four independent harmonic coefficients are given by:

$$f_0 = \frac{1 - \cos\Gamma}{2} f_{a0} + \frac{1 + \cos\Gamma}{2}(f_{p0} + f_{p1}\cos 2P + f_{p2}\sin 2P) \quad (Eq. 6)$$

$$f_1 = -(M_{30} + M_{31}\cos 2P - M_{32}\sin 2P)\sin\Gamma$$

$$f_3 = \frac{1 - \cos\Gamma}{2}(f_{a1}\cos 2A + f_{a2}\sin 2A)$$

$$f_4 = \frac{1 - \cos\Gamma}{2}(f_{a1}\sin 2A + f_{a2}\cos 2A)$$

where the retardation of the compensator (i.e., waveplate), $\Gamma$, is related to the polarizing transmission coefficient ($t_p$, $t_s$), $e^{j\Gamma}=\tau=t_p/t_s$. The coefficients of Eq. 6 are given by:

$f_{p0} = M_{00} + M_{10} \cos 2A - M_{20} \sin 2A$ $f_{p1} = M_{01} + M_{11} \cos 2A - M_{21} \sin 2A$ $f_{p2} = -(M_{02} + M_{12} \cos 2A - M_{22} \sin 2A)$ $f_{a0} = M_{00} + M_{01} \cos 2P - M_{02} \sin 2P$ $f_{a1} = M_{10} + M_{11} \cos 2P - M_{12} \sin 2P$ $f_{a2} = -(M_{20} + M_{21} \cos 2P - M_{22} \sin 2P) \quad (Eq. 7)$ Utilizing these coefficients and their relationship to the associated Mueller matrix components, the RCSE mode of the system 100 may be fully calibrated.

Figure 1D:
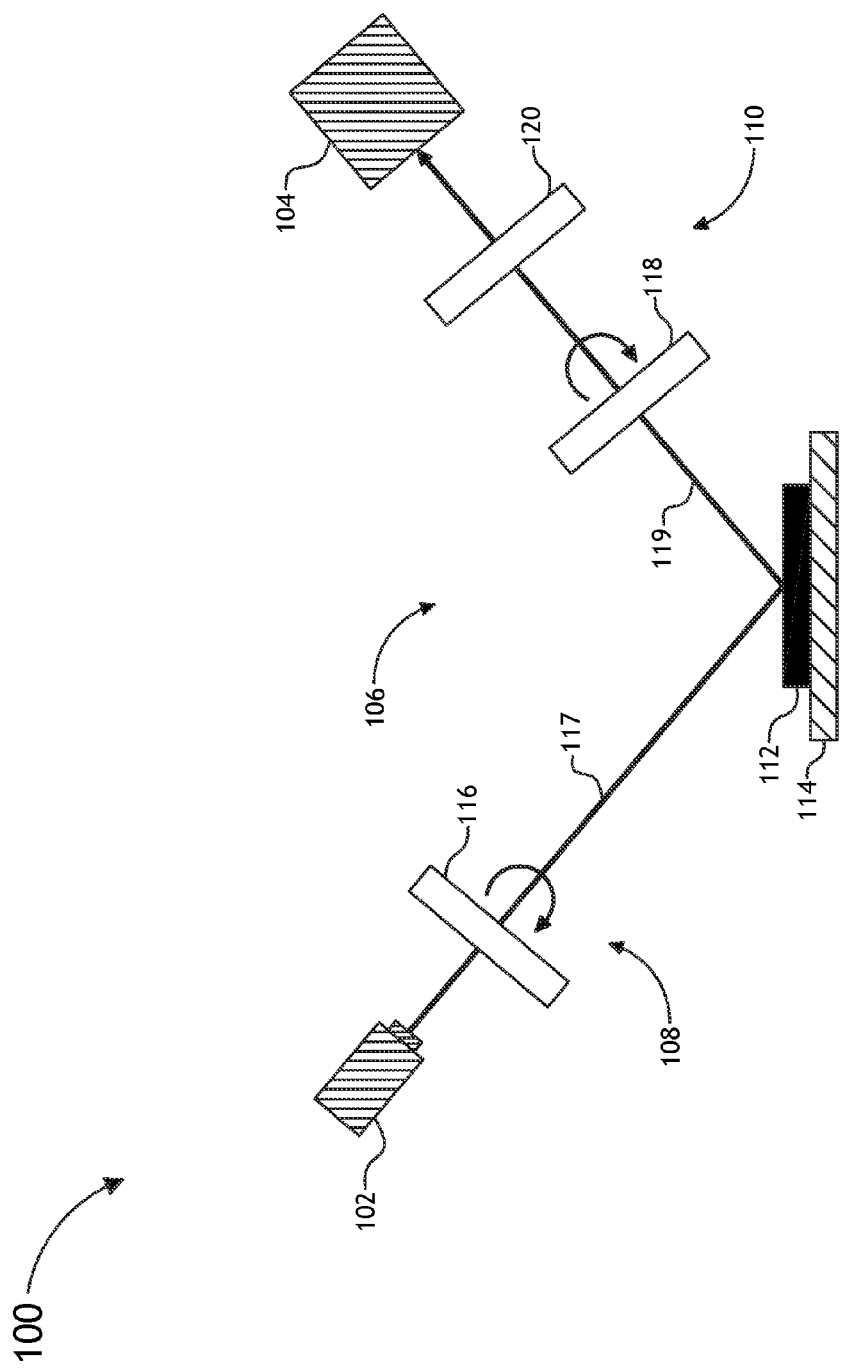
FIG. 1D illustrates a schematic view of a rotating polarizer-rotating compensator spectroscopic ellipsometry (RPRC SE) mode of the selectably configurable MMSE system, in accordance with one embodiment of the present invention.

FIG. 1D illustrates the rotating polarizer-rotating compensator spectroscopic ellipsometry (RPRC SE) mode of the system 100. In the RPRC SE mode, the compensator is "flipped in" the collection pathway 119 of the collection arm 110, with the polarizer positioned along the illumination pathway 117 of the illumination arm 108. In addition, both the compensator and polarizer are rotating at constant angular frequency. The compensator is rotating at constant angular frequency, $\omega_c$, while the polarizer is rotating at constant angular frequency, $\omega_p$.

It is recognized herein that in addition to measuring certain off-diagonal Mueller elements, the RPRC SE Mueller configuration is also capable of improved system calibration using additional system parameters. One group of the critical system parameters includes the polarization properties of the compensator (i.e., waveplate). Traditionally, the waveplate compensator is considered "ideal," whereby only the polarizing phase (the retardation) is used to characterize the waveplate. In practice, however, proper characterization of the compensator waveplate requires quantification of the so called "diattenuation" or "dichroism." In this regard, retardation of the compensator (i.e., waveplate), $\Gamma$, is related to the polarizing transmission coefficient by: $e^{j\Gamma}=\tau=t_p/t_s$. Equivalently, the compensator waveplate may be described using the following three parameters:

$$s = \frac{1 - |\tau|^2}{1 + |\tau|^2} \ll 1 \quad (Eq. 8)$$

$$p = \frac{2|\tau|\cos\Gamma}{1 + |\tau|^2}$$

$$r = \frac{2|\tau|\sin\Gamma}{1 + |\tau|^2}$$

Utilizing the parameters of equation 8, the detector signal in the RPRC SE mode may be expressed in terms of a linear combination of harmonics of both the polarizer and compensator angular frequencies. The detector signal is provided by:

$$S_D = S_F \begin{bmatrix} f_0 + f_1\cos 2\omega_p t + f_2\sin 2\omega_p t + f_3\cos 2\omega_c t + f_4\sin 2\omega_c t + \\ f_5\cos 2(\omega_p - \omega_c)t + f_6\sin(2\omega_p - 2\omega_c)t + \\ f_7\cos 2(\omega_p + \omega_c)t + f_8\sin 2(\omega_p + \omega_c) + t + f_9\cos 4\omega_c t + \\ f_{10}\sin 4\omega_c t \\ f_{11}\cos(2\omega_a - 4\omega_c)t + f_{12}\sin(2\omega_a - 4\omega_c)t + \\ + f_{13}\cos(2\omega_a + 4\omega_c)t + f_{14}\sin(2\omega_a - 4\omega_c)t \end{bmatrix} \quad (Eq. 9)$$

where the harmonic coefficients of equation 9 may be related to the system and sample parameters by:

$$f_0 = \frac{1-p}{2}M_{00} + \frac{1+p}{2}f_{p0} \quad (Eq. 10)$$

$$f_1 = \frac{1-p}{2}M_{01} + \frac{1+p}{2}f_{p1}$$

$$f_2 = -\frac{1-p}{2}M_{02} + \frac{1+p}{2}f_{p2}$$

$$f_3 = -rM_{30}\sin 2A + s(M_{10} + M_{00}\cos 2A)$$

$$f_4 = rM_{30}\cos 2A - s(M_{20} - M_{00}\sin 2A)$$

$$f_5 = \frac{-r(M_{31}\sin 2A + M_{32}\cos 2A) +}{2} \frac{s(M_{11} + M_{22} + M_{01}\cos 2A - M_{02}\sin 2A)}{2}$$

$$f_6 = \frac{r(M_{32}\sin 2A - M_{31}\cos 2A) -}{2} \frac{s(M_{12} - M_{21} + M_{01}\sin 2A + M_{02}\cos 2A)}{2}$$

-continued $$f_7 = \frac{\begin{array}{c}-r(M_{31}\sin2A - M_{32}\cos2A) + \\ s(M_{11} - M_{22} + M_{01}\cos2A + M_{02}\sin2A)\end{array}}{2}$$

$$f_8 = \frac{\begin{array}{c}r(M_{32}\sin2A + M_{31}\cos2A) - \\ s(M_{12} + M_{21} - M_{01}\sin2A + M_{02}\cos2A)\end{array}}{2}$$

$$f_9 = \frac{1-p}{2}(M_{10}\cos2A + M_{20}\sin2A)$$

$$f_{10} = \frac{1-p}{2}(M_{10}\sin2A - M_{20}\cos2A)$$

$$f_{11} = \frac{1-p}{4}[(M_{11} + M_{22})\cos2A - (M_{12} - M_{21})\sin2A]$$

$$f_{12} = -\frac{1-p}{4}[(M_{12} - M_{21})\cos2A + (M_{11} + M_{22})\sin2A]$$

$$f_{13} = \frac{1-p}{4}[(M_{11} - M_{22})\cos2A + (M_{12} + M_{21})\sin2A]$$

$$f_{14} = -\frac{1-p}{4}[(M_{12} + M_{21})\cos2A - (M_{11} - M_{22})\sin2A]$$

In addition to providing multiple selectable modes of spectroscopic ellipsometry, the system 100 of the present disclosure further provides enhanced calibration capabilities. In the case of the RPSE mode, the calibration of the system 100 is relatively straightforward due to the relative simplicity of RPSE. The most critical parameters, such as wavelength as a function of detector pixel, angle of incidence (AOI) of illumination on the sample 112, the polarizer home position, the analyzer angle, and the azimuth angle of the plane of incidence relative to a sample of grating lines, may be systematically calibrated.

In the case of the RCSE mode, calibration becomes more difficult. Difficulty in calibration in the RCSE mode arises from the fact that the retardation of the compensator waveplate 118 is function of illumination wavelength. The difficulty is further compounded by the fact that in the RCSE mode the compensator waveplate serves as a critical component of the optical system 106, with the compensator rotating at a constant frequency, $\omega_c$. As such, errors in calibration may significantly impact measurement performance of the system 100.

In one aspect of the present invention, the multimode system 100 may be used to calibrate compensator retardation at each wavelength of illumination. In this regard, a calibration sample (wafer), consisting of a single-layer film stack, may be implemented for the purposes of calibrating the system 100. In one embodiment, the calibration wafer may include a single-layer film stack of silicon dioxide disposed on a silicon substrate. Since the calibration is isotropic, the Mueller matrix associated with the calibration sample may be simplified as:

$$M_{sample} = \begin{bmatrix} M_{00} & M_{01} & 0 & 0 \\ M_{10} & M_{11} & 0 & 0 \\ 0 & 0 & M_{22} & M_{23} \\ 0 & 0 & M_{32} & M_{33} \end{bmatrix} \quad (Eq.\ 11)$$

where the components of the simple matrix are given by:

$$M_{11} = M_{00} = \frac{R_p + R_s}{2} \quad (Eq.\ 12)$$

$$M_{10} = M_{01} = \frac{R_p - R_s}{2}$$

$$M_{22} = M_{33} = \sqrt{R_p R_s}\,\cos\Delta$$

$$M_{23} = -M_{32} = \sqrt{R_p R_s}\,\sin\Delta$$

As such, the harmonics associated with the RPRC Mueller SE mode of the system 100 may then be written as:

$$f_0 = \frac{R_p + R_s}{2} + \frac{1+p}{4}(R_p - R_s)\cos2A \quad (Eq.\ 13)$$

$$f_1 = \frac{R_p - R_s}{2} + \frac{1+p}{4}(R_p + R_s)\cos2A$$

$$f_2 = \frac{1+p}{2}\sqrt{R_p R_s}\,\cos\Delta\sin2A$$

$$f_3 = s\left(\frac{R_p - R_s}{2} + \frac{R_p + R_s}{2}\cos2A\right)$$

$$f_4 = s\frac{R_p + R_s}{2}\sin2A$$

$$f_5 = \frac{r\sqrt{R_p R_s}\,\sin\Delta}{2}\cos2A +$$
$$s\left(\frac{R_p + R_s}{4} + \frac{\sqrt{R_p R_s}\,\cos\Delta}{2} + \frac{R_p - R_s}{4}\cos2A\right)$$

$$f_6 = -\left(\frac{r\sqrt{R_p R_s}\,\sin\Delta}{2} + s\frac{R_p - R_s}{4}\right)\sin2A$$

$$f_7 = -\frac{r\sqrt{R_p R_s}\,\sin\Delta}{2}\cos2A +$$
$$s\left(\frac{R_p + R_s}{4} - \frac{\sqrt{R_p R_s}\,\cos\Delta}{2} + \frac{R_p - R_s}{4}\cos2A\right)$$

$$f_8 = -\left(\frac{r\sqrt{R_p R_s}\,\sin\Delta}{2} - s\frac{R_p - R_s}{4}\right)\sin2A$$

$$f_9 = \frac{1-p}{4}(R_p - R_s)\cos2A$$

$$f_{10} = \frac{1-p}{4}(R_p - R_s)\sin2A$$

$$f_{11} = \frac{1-p}{4}\left(\frac{R_p + R_s}{2} + \frac{\sqrt{R_p R_s}\,\cos\Delta}{2}\right)\cos2A$$

$$f_{12} = -\frac{1-p}{4}\left(\frac{R_p + R_s}{2} + \frac{\sqrt{R_p R_s}\,\cos\Delta}{2}\right)\sin2A$$

$$f_{13} = \frac{1-p}{4}\left(\frac{R_p + R_s}{2} - \frac{\sqrt{R_p R_s}\,\cos\Delta}{2}\right)\cos2A$$

$$f_{14} = \frac{1-p}{4}\left(\frac{R_p + R_s}{2} - \frac{\sqrt{R_p R_s}\,\cos\Delta}{2}\right)\sin2A$$

It is noted herein that utilizing an analyzer 120 angle of 0° or 45° results in the removal of some dependent harmonics. As such, equation 13 may reduce to:

$$f_0 = \frac{R_p + R_s}{2} + \frac{1+p}{4}(R_p - R_s) \quad (Eq.\ 14)$$

$$f_1 = \frac{R_p - R_s}{2} + \frac{1+p}{4}(R_p + R_s)$$

$$f_2 = (1+p)\delta_a\sqrt{R_p R_s}\,\cos\Delta$$

-continued $$f_3 = R_p s$$

$$f_4 = (R_p + R_s)(s\delta_a) \to 0$$

$$f_5 = \frac{r\sqrt{R_p R_s}\sin\Delta + s(R_p + \sqrt{R_p R_s}\cos\Delta)}{2}$$

$$f_6 = -r\delta_a\sqrt{R_p R_s}\sin\Delta$$

$$f_7 = \frac{-r\sqrt{R_p R_s}\sin\Delta + s(R_p - \sqrt{R_p R_s}\cos\Delta)}{2}$$

$$f_8 = f_6$$

$$f_9 = \frac{1-p}{4}(R_p - R_s)$$

$$f_{10} = f_9 \delta_a$$

$$f_{11} = \frac{1-p}{4}\left(\frac{R_p + R_s}{2} + \frac{\sqrt{R_p R_s}\cos\Delta}{2}\right)$$

$$f_{12} = -f_{11}\delta_a$$

$$f_{13} = \frac{1-p}{4}\left(\frac{R_p + R_s}{2} - \frac{\sqrt{R_p R_s}\cos\Delta}{2}\right)$$

$$f_{14} = f_{13}\delta_a$$

In turn, a user or the control system 107 may calibrate one or more of the parameters of the system 100. For example, parameters suitable for calibration may include, but are not limited to, deviation of the analyzer angle, $\delta_a$ (measured from zero), the compensator dichroism-related parameter s, and the parameter related to the real part of the compensator retardation, p. Each of these parameters may be expressed in terms of the coefficients from Eq. 14 as follows:

$$\delta_a = \frac{1}{6}\left(\frac{f_{10}}{f_9} - \frac{f_{12}}{f_{11}} + \frac{f_{14}}{f_{13}}\right) \quad \text{(Eq. 15)}$$

$$p = \frac{2f_0 - f_1 - 3(f_{11} + f_{13})}{f_1 + f_{11} + f_{13}}$$

$$s = \frac{3+p}{2}\frac{f_3}{f_0 + f_1}$$

It is noted herein that the parameter, r, related to the imaginary part of the compensator retardation cannot be directly solved using equation 14 as it is always combined with the imaginary part of the sample ellipsometric parameter, sin Δ. However, the r-parameter may be solved indirectly using the s- and p-parameters of Eq. 15. In addition, the r-parameter may be determined independently utilizing the RCSE mode of the multimode system 100.

In one aspect, the r-parameter may be determined utilizing information from a calibration sample, described previously herein. For example, single layer film stacks, such as a single layer of silicon dioxide film, having thicknesses of approximately 200 Å, have been widely used for calibration purposes. Based on measurements from such a calibration sample, it is possible to eliminate the 180° uncertainty in the polarizing phase term. In this regard, it is known at each wavelength whether the phase term Δ of ellipsometric parameter (tan Δ=|$r_p/r_s$|, where Δ=Arg[$r_p/r_s$]) of the sample is in the [0, 180] region, or the [180, 360] region. Based on this information, it is possible to eliminate the 180° uncertainty in the compensator retardation. As a result, one may use these equations to over-determine sample ellipsometric parameters:

$$\frac{R_p - R_s}{R_p + R_s} = \frac{(3+p)f_9}{2f_0 - (1+p)f_1} \quad \text{(Eq. 16)}$$

$$\frac{R_s}{R_p + R_s} = \frac{(3+p)(f_{11} + f_{13} - f_9)}{4f_0 - 2(1+p)f_1}$$

$$\frac{R_p}{R_p + R_s} = \frac{(1-p)(f_0 + f_1)}{4f_0 - 2(1+p)f_1}$$

$$\frac{\sqrt{R_p R_s}\cos\Delta}{R_p + R_s} = \frac{1}{2}\frac{f_{11} - f_{13}}{f_{11} + f_{13}}$$

where equation (16) acts to over-determine the ellipsometric parameters, $R_p$, $R_s$, cos Δ, and sin Δ. As a result, utilizing the known ellipsometric parameters the compensator spectral retardation r is provided by:

$$r\tan\Delta = \frac{(1-p)(f_5 - f_7)}{2(f_{11} - f_{13})} - s \quad \text{(Eq. 17)}$$

$$r\frac{\sqrt{R_p R_s}\sin\Delta}{R_p + R_s} = \frac{(3+p)(1-p)}{4}\frac{f_5 - f_7}{2f_0 - (1+p)f_1} - \frac{s}{2}\frac{f_{11} - f_{13}}{f_{11} + f_{13}}$$

An overview of the relationship between various ellipsometric parameters as well as the principles of ellipsometry is provided generally in Harland G. Tompkins and Eugene A. Irene, *Handbook of Ellipsometry*, 1st ed, William Andrew, Inc., 2005, which is incorporated herein by reference in the entirety. In addition, Mueller matrix ellipsometry in the context of imperfect compensators is discussed in detail in P. S. Hauge, *Mueller Matrix Ellipsometry with Imperfect Compensators*", J. of the Optical Soc. of Am. A 68(11), 1519-1528, 1978, which is incorporated herein in its entirety. Mueller matrix ellipsometry in the context of rotating polarizer and analyzer is discussed in detail in R. M. A Azzam, *A Simple Fourier Photopolarimeter with Rotating Polarizer and Analyzer for Measuring Jones and Mueller Matrices*, Opt Comm 25(2), 137-140, 1978, which is incorporated herein in its entirety. Further, the concept of "complete" ellipsometry is discussed in M. L. Aleksandrov, et. al. "*Methods and Apparatus for Complete Ellipsometry (review)*", J. Appl. Spectroscopy 44(6), 559-578, 1986, which is incorporated herein in its entirety.

In another aspect of the present invention, upon calibration of the various system 100 parameters, the multimode system 100 may then be utilized to carry out spectroscopic ellipsometry measurements on one or more test samples. The determination of the ellipsometric parameters, such as p, s, $\delta_a$, and r provides for improved precision, accuracy, stability, tool-to-tool matching. In addition, the multimode system 100 provides for improved baseline matching. The ability to configure system 100 in multiple ellipsometric modes allows for unique measurement capabilities, which are further amplified due to the improved calibration abilities of the system 100.

Figure 2A:
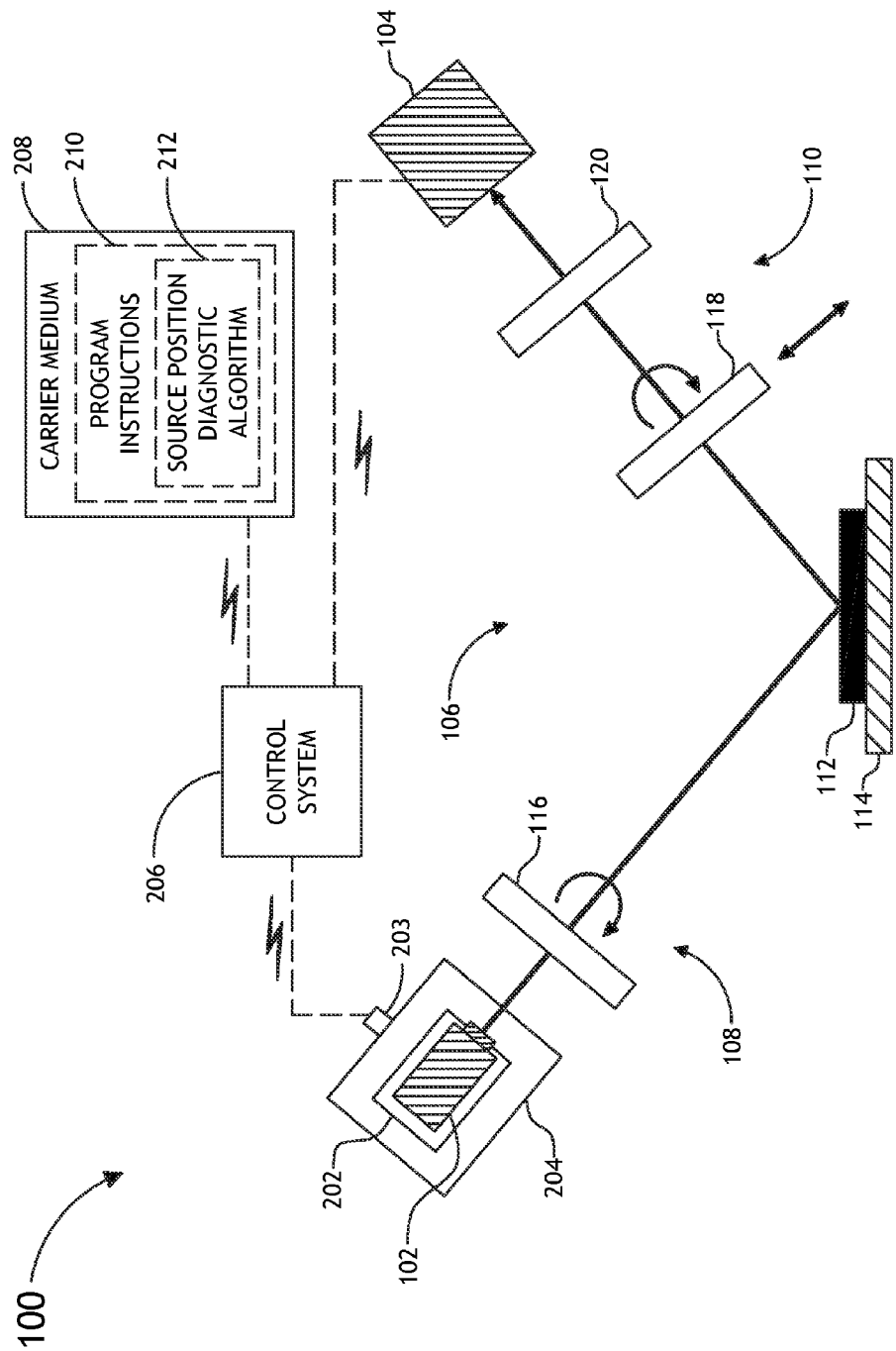
FIG. 2A illustrates a schematic view of a selectably configurable multimode MMSE system equipped with an illumination tracking and adjustment sub-system, in accordance with one embodiment of the present invention.

FIG. 2A illustrates the multimode spectroscopic ellipsometer equipped with beam tracking capabilities in a direct-coupled illumination setting, in accordance with an alternative embodiment of the present invention.

It is recognized herein that long term stability of the multimode SE system 100 may be measured using measurement results acquired over a period of extended time, such as weeks or months. In this manner, the stability of the measurement system may be acquired and monitored by analyzing measurement results obtained under identical measurement conditions (e.g., identical recipes) as a function of time. Those skilled in the art will further recognize that changes in the measurement results as a function of time may be influenced by numerous factors. The factors may include, but are not limited to, illumination source position relative to the optical system, slow decay of illumination source intensity, and changes in sample conditions, such as changes in optical properties of the measured sample (e.g., optical changes due to accumulated UV exposure).

In one embodiment of the present invention, the system 100 may include a means for active tracking of the illumination source 102. Application of an active illumination source tracking function may enable the system 100 to adjust the spatial positioning of the illumination source 102 relative to the various optical components of the measurement system 100. It is contemplated herein that the active illumination source tracking function may be executed via a closed-loop feedback operation.

As shown in FIG. 2A, the multimode SE system 100 may further include a multi-axis actuation stage 202 of a multi-axis actuation control system 204 configured to actuate the illumination source 102 in response to determined illumination source 102 drift. The system 100 may further include a computer control system 206 communicatively coupled to the actuation control system 204 and the detector 104. The computer control system 206 may be configured to receive one or more signals from the detector 104 indicative of intensity measurement data obtained from a diagnostic sample loaded on the sample stage 114. The computer control system 206 may further be configured to transmit one or more instruction signals to the multi-axis actuation control system 204 based on a source position diagnostic algorithm 212, as will be discussed in greater detail further herein. In the embodiment of FIG. 2A, the optical system 106 is configured to direct-couple the illumination source 102 and the detector 104.

In one embodiment of the present invention, the multi-axis actuation stage 202 may include any actuation stage known in the art. For example, the multi-axis actuation stage 202 may include a translational stage or rotational stage. For instance, the multi-axis actuation stage 202 may include, but is not limited to, a motorized translation stage. In another instance, the multi-axis actuation stage 202 may include, but is not limited to, a motorized rotational stage. It is further contemplated herein that the multi-axis actuation stage 202 may consist of a stage having both translational and rotational capabilities.

In a further embodiment, the multi-axis actuation stage 202 may include any stage known in the art capable of responding to a control system from one or more computer systems 206. In this sense, the multi-axis actuation stage 202 may be configured to receive command signals either directly or indirectly from the one or more computer systems 206. For example, the multi-axis actuation stage 202 may be communicatively coupled to the computer control system 206, allowing the computer control system 206 to directly control the multi-axis actuation stage 202. In another example, the multi-axis actuation control system 204 may control the multi-axis actuation stage 202 using information transmitted from the one or more computer systems 206 to the multi-axis actuation control system 204.

In another aspect of the present invention, the computer control system 206 may be configured to execute a source position diagnostic algorithm 212 utilizing information received from a diagnostic sample by the detector 104. In this manner, the detector 104 may acquire a set of intensity measurement data associated with light reflected from a diagnostic sample loaded onto the sample stage 114.

Those skilled in the art will recognized that the measured intensity of the light reflected from the sample 112 (e.g., diagnostic sample) may vary with respect to a variety of parameters. For example, in the case of the RPSE mode of the multimode system 100, the measured intensity of illumination is expressed by:

$$I = I_0(\alpha \cdot \cos 2P + \beta \cdot \sin 2P) \quad \text{(Eq. 18)}$$

$$P = \omega_P \cdot t \quad \text{(Eq. 19)}$$

where I represents the measured intensity by the detector 104, $I_0$ represents the intensity of the light emanating from the illumination source 102, P represents the polarizer angle, and $\omega_p$ again represents the polarizer angular frequency.

Figure 2B:
FIG. 2B illustrates a schematic view of a thin film based diagnostic sample suitable for implementation in the sub-system for tracking and adjusting illumination source position drift in the MMSE system, in accordance with one embodiment of the present invention.
Figure 2C:
FIG. 2C illustrates a schematic view of a patterned grating based diagnostic sample suitable for implementation in the sub-system for tracking and adjusting illumination source position drift in the MMSE system, in accordance with one embodiment of the present invention.

As shown in FIGS. 2B and 2C, the diagnostic sample utilized to acquire the diagnostic parameters may include a sample engineered to have a selected set of properties. In one embodiment, the diagnostic sample may include, but is not limited to, a thin film sample 214, having known properties such as, but not limited to, thickness and index of refraction(s). For example, the thin film sample 214 may include a simple film 216 deposited on a substrate 218. For instance, the thin film 216 may consist of a first layer of material and a second layer, each with known properties.

In a further embodiment, it is contemplated that the diagnostic sample utilized to perform the illumination tracking function of the illumination source 102 of the multimode SE system 100 may be the same sample as the calibration sample utilized to perform the calibration function of one or more ellipsometric parameters of the multimode SE system 100. In this regard, a simple film sample may be fabricated to have a selected set of properties (e.g., thickness, index of refraction, and etc.), while also being suitable for calibrating one or more of the ellipsometric parameters of the system 100.

In another embodiment, the diagnostic sample may include, but is not limited to, a patterned grating sample 220 deposited on a substrate. For example, the patterned grating sample 220 may be constructed to possess a set of selected characteristics. For instance, the selected characteristics of the patterned grating sample 220 may include, but are not limited to, a selected critical dimension (CD) 222, a selected side-wall angle (SWA) 224, a selected feature height 226, or a selected feature periodicity (d) 228.

Upon receiving the measurement results associated with the chosen diagnostic sample, the computer control system 206 may acquire a set of diagnostic parameters utilizing the source position diagnostic algorithm 212. The measured set of diagnostic parameters may then be compared to an initial set of diagnostic parameters obtained from the diagnostic sample at an initial set of alignment conditions (e.g., optimal or near-optimal alignment conditions) in order to determine the magnitude of the illumination source 102 position change. In this sense, the computer control system 206 may compare diagnostic parameters extracted from intensity data of the diagnostic sample to archived diagnostic sample imagery data taken at an earlier time. For instance, the archived imagery data of the diagnostic sample may be saved in the memory of the computer. Further, it is recognized herein that the archived imaged data of the diagnostic sample may represent imagery data of the diagnostic sample obtained at optimum alignment conditions.

It is recognized herein that the illumination source 102 position drift, which occurs over time, may manifest itself in the measured light intensity data as well as the measured diagnostic parameters. While the source intensity is a convolution of normal illumination source 102 intensity decay and illumination source 102 position drift relative to the measurement optics of system 100, it is recognized herein that the diagnostic parameters are a gauge of the illumination source 102 position drift. As such, the diagnostic parameters (when compared to diagnostic parameters obtained at initial alignment conditions) may be utilized to monitor and compensate for the illumination source 102 position drift and change in illumination source 102 intensity spectral-spatial distribution. It is noted herein that source position drift may also induce spectral distribution changes on the sample.

In the case of the thin film sample 214, the one or more diagnostic parameters that may be extracted may include, but are not limited to, total intensity integrated over a selected spectral range (e.g., intensity integrated over a broad spectrum range), the polarizer asymmetry parameter, or the percentage of higher harmonic components (commonly referred to as "4P"), or relative intensity ratio of DUV to NIR. Each of these diagnostics parameters may be computationally extracted from the spectra obtained from the thin film sample 214 utilizing the computer control system 206. After these diagnostic parameters are extracted they may be compared to the diagnostic parameters extracted from the diagnostic sample at an alignment condition (e.g., optimal alignment condition) in order to determine the magnitude of the illumination source 102 drift relative to the initial alignment condition.

In the case of the patterned grating sample 220, diagnostic parameters may be extracted from the acquired spectrum by comparing the experimental data to an accepted theoretical model. In this manner, the experimental data may be regressed against the theoretical model, allowing for the extraction of the diagnostic parameters by the computer control system 206. It is recognized herein that, in the event the position of the illumination source shifts relative to an initial measurement instance, the regressed diagnostic parameters, such as SWA, CD, and periodicity of the grated sample 220, may deviate from the diagnostic parameters measured during the initial measurement, allowing the system 100 to determine the magnitude of the illumination source 102 drift. It is noted herein that the pattern of sample 220 may include a three-dimensional pattern. Further, it is recognized that the pattern need not be symmetric in nature and may include an asymmetric pattern.

Upon determining the magnitude of the illumination source 102 drift, the one or more computer systems 206 may then determine the direction of the illumination source position drift. The computer control system 206 may transmit one or more instruction signals to the multi-axis actuation control system 204 in order to actuate (e.g., translate) the illumination source 102 (via the actuation stage 202) by the determined magnitude of illumination source position drift in a first direction within the optical plane and in a second direction perpendicular to the optical plane, as well as tip and tilt. In this sense, the detector 104 may measure intensity changes as a function of the directed actuation from the computer control system 206 and transmit those changes to the computer control system 206. The computer control system 206 may then deduce the direction of the illumination source 102 position drift utilizing the measurement results from the detector 104.

Upon determining both the magnitude and direction of illumination source 102 position drift, the computer control system 206 may transmit a set of illumination source position adjustment parameters to the multi-axis actuation control system 204 via input 203 of the multi-axis actuation control system 204. In turn, the multi-axis actuation control system 204 may adjust the position of the multi-axis actuation stage 202 in accordance with the adjustment parameters provided by the computer control system 206. In this regard, the adjustment parameters may be used by the multi-axis actuation control system 204 and the multi-axis stage 202 to compensate for illumination source drift and/or changes in illumination spectral-spatial distribution.

It is further contemplated herein that upon compensating for the illumination source position drift and/or changes in illumination spatial distribution, the system 100 may repeat the diagnostic sequence described above. In this manner, the computer control system 206 may repeat the source position diagnostic algorithm 212 in an effort to refine the compensation of the illumination source position drift until a selected level of compensation is attained.

It should be recognized that the various steps described throughout the present disclosure with respect to FIGS. 2A-2C may be carried out by a single computer control system 206 or, alternatively, a multiple computer control system 206. Moreover, different subsystems of the system 100, such as the multi-axis actuation control system 204, may include a computer system suitable for carrying out at least a portion of the illumination source tracking/correction steps described above. Therefore, the above description should not be interpreted as a limitation on the present invention but merely an illustration. Further, the one or more computer systems 206 may be configured to perform any other step(s) of any of the method embodiments described herein.

It is further recognized that computer control system 206 and the computer control system 107 described previously herein may consist of the same computational unit. While described independently above, it is contemplated that the computer control system 206 and control system 107 may function as a single computational system. In another embodiment, the control system 206 and the control system 107 may be communicatively coupled to one another. In yet another embodiment, the control system 206 and control system 107 may be themselves controlled by an additional control system (not shown). In this regard, control system 206 and control system 107 may be embodied as computational modules existing in a higher-level computational and operational infrastructure (i.e., system including multiple computers and multiple functional capabilities).

In another embodiment, the computer control system 206 may be communicatively coupled to the multi-axis actuation control system 204 or detector 104 in any manner known in the art. For example, the computer control system 206 may be communicatively coupled to the multi-axis actuation control system 204 or the detector via a wireline or wireless connection.

For example, the one or more control systems 206 may be coupled to a computer system of the multi-axis actuation control system 204. Moreover, the computer control system 206 of the system 100 may be configured to receive and/or acquire data or information from other systems by a transmission medium that may include wireline and/or wireless portions. In this manner, the transmission medium may serve as a data link between the computer control system 206 and other subsystems of the system 100. Moreover, the computer control system 206 may send data to external systems via a transmission medium.

The computer control system 206 may include, but is not limited to, a personal computer system, mainframe computer system, workstation, image computer, parallel processor, or any other device known in the art. Program instructions 210 for implementing methods illumination drift tracking and adjustment may be transmitted over or stored on carrier medium 208. The carrier medium 208 may be a transmission medium such as a wire, cable, or wireless transmission link. The carrier medium may also include a storage medium such as a read-only memory, a random access memory, a magnetic or optical disk, or a magnetic tape.

Figure 3A:
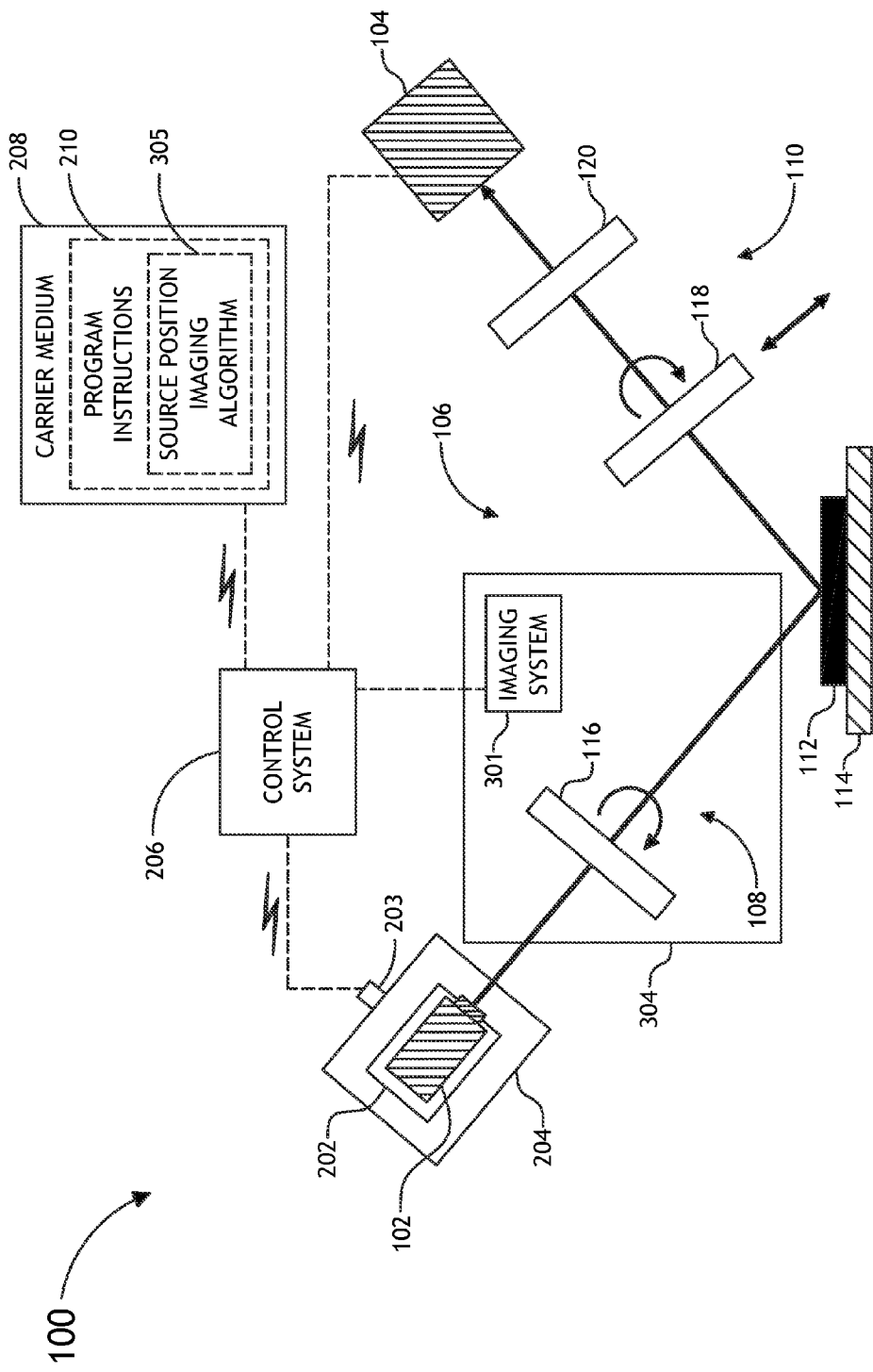
FIG. 3A illustrates a schematic view of a selectably configurable multimode MMSE system equipped with a direct imaging sub-system for tracking and adjusting illumination source position drift in the MMSE system, in accordance with one embodiment of the present invention.
Figure 3B:
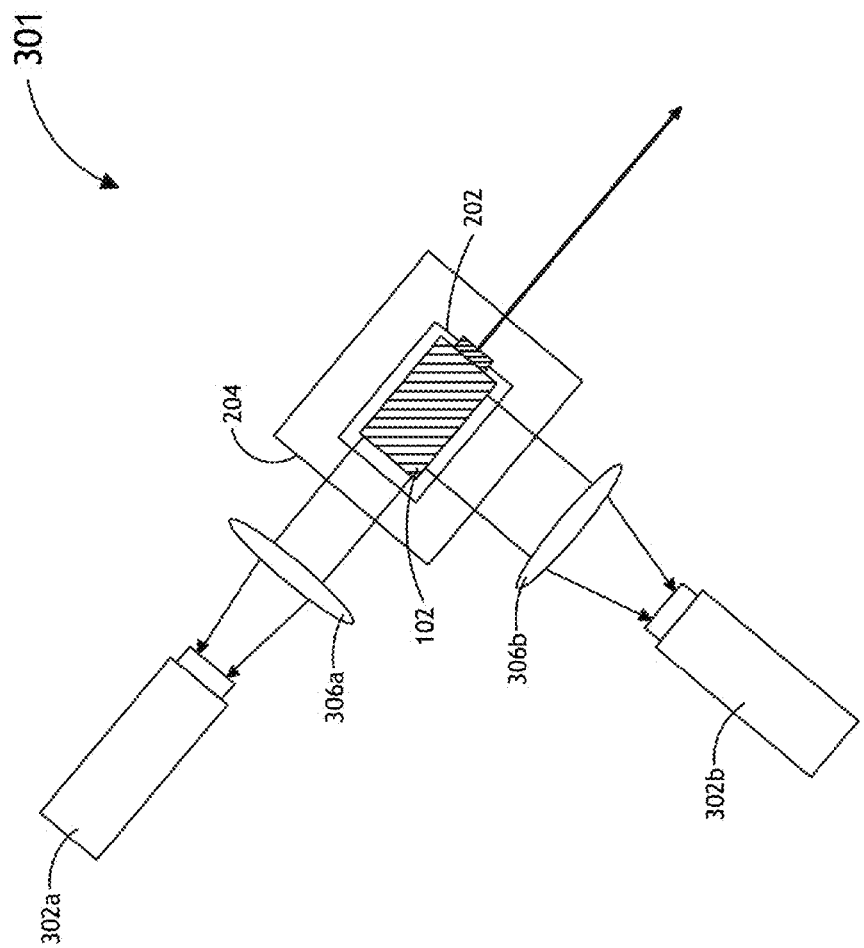
FIG. 3B illustrates a schematic view of a direct imaging sub-system equipped with two cameras and a translatable multi-axis sample stage suitable implementation in the MMSE system, in accordance with one embodiment of the present invention.

FIGS. 3A and 3B illustrate a schematic view of the multi-mode SE system 100 equipped with image-based illumination source drift tracking and adjusting functionality, in accordance with an alternative embodiment of the present invention. In one aspect, the system 100 may include a direct imaging system 301 configured to measure the position of an illumination source 102 or the spatial distribution of the light intensity of illumination emanating from the illumination source 102.

In a further aspect, the direct imaging system 301 is communicatively coupled to the computer control system 206 of the system 100. In this manner, the direct imaging system 301 may be configured to transmit one or more sets of imagery data to the computer control system 206. The sets of imagery data may include imagery data associated with the position of the illumination source 102 or the spectral-spatial distribution of the illumination intensity of the light emitted by the illumination source. In this manner, the direct imaging system 301 may acquire one or more sets of imagery data of the illumination source 102. Upon acquiring the imagery data of the illumination source, the direct imaging system 301 may transmit a signal indicative of the imagery data to the computer control system 206.

Upon receiving the imagery data from the direct imaging system 301, the computer control system 206 may compare the acquired imagery data of the illumination source 102 to imagery data of the illumination source obtained in a preferred alignment condition. In this sense, the imagery data of the illumination source obtained while the illumination source is in a preferred alignment condition may be referred to as "reference imagery data." For example, the computer control system 206 may compare the acquired imagery data of the illumination source 102 to imagery data (i.e., reference imagery data) of the illumination source 102 as it existed in an optimal or near-optimal alignment condition. The comparison data created by comparing the acquired imagery data and the reference imagery data may then be utilized to determine the magnitude and direction of the position drift of the illumination source 102 relative to the various optical element of the optical system 106. In a further aspect, the reference imagery data may be stored in the memory of the computer control system 206. In this regard, the acquired imagery data may be compared to the stored reference imagery data in order to measure the amount of position drift and/or the direction of position drift of the illumination source 102. It is recognized herein that the various sets of imagery data described throughout the present disclosure may be stored in the memory of the computer control system 206 or a portable memory means (e.g., CD, DVD, flash drive, portable hard drive, communicatively couple server or the like) in any digital image format known in the art.

It is contemplated herein in that the computer control system 206 may execute a pre-programmed source position imaging algorithm 305 suitable for comparing the acquired images of the illumination source 102 and the reference images of the illumination source 102. In turn, the source position imaging algorithm 305 may extract magnitude and direction information of the illumination source 102 drift.

Upon determining the magnitude and direction of position drift of the illumination source 102, the computer control system 206 may determine a set of position adjustment parameters suitable for use by the multi-axis actuation stage 202 of the multi-axis actuation control system 204. In this sense, the computer control system 206 may calculate the adjustment parameters utilizing the determined position drift of the illumination source 102. For example, the computer control system 206 may calculate the adjustment parameters required to compensate for the magnitude and direction of the position drift of the illumination source 102. It is recognized herein that the specific form of the adjustment parameters may depend on the specific type of multi-axis actuation stage 202 employed. For instance, in the event an X-Y translation stage is employed, the adjustment parameters may form a set of displacement values in the X- and Y-directions required to compensate for the position drift. In another instance, in a rotational stage setting, the adjustment parameters may, in part, include a rotational component and radial component required to compensate for the position drift of the illumination source. It is further contemplated herein that the multi-axis actuation stage 202 may include three-dimensional actuation capabilities. In this setting, the adjustment parameters may include displacement components in three dimensions (e.g., X-direction, Y-direction, and Z-direction). In yet another instance, the translational and rotational movement could be coupled to in order to provide increased adjustment flexibility to meet the stringent system measurement requirements.

Upon calculating the set of illumination source position adjustment parameters, the computer control system 206 may transmit the set of illumination source position adjustment parameters to the multi-axis actuation control system 204 via the input 203 of the multi-axis actuation control system 204. In turn, the multi-axis actuation control system 204 system may adjust the position of the multi-axis actuation stage 202 in accordance with the adjustment parameters provided by the computer control system 206. In this regard, the adjustment parameters may be used by the multi-axis actuation control system 204 and the multi-axis actuation stage 202 to compensate for illumination source drift and/or changes in illumination spectral-spatial distribution.

It is further contemplated herein that upon compensating for the illumination source position drift and/or changes in illumination spatial distribution, the system 100 may repeat the source position drift determination sequence described above. In this manner, the computer control system 206 may repeat the source position imaging algorithm 305 in an effort to refine the compensation of the illumination source position drift.

In one embodiment, the direct imaging system 301 may include a camera. It is recognized herein that a camera of the direct imaging system 301 may include any camera or camera system known in the art. For example, the camera of the direct imaging system 301 may include a charged coupled device (CCD) base camera. In a further embodiment, a DUV band pass filter may be positioned in front of the camera in order to aid in the determination of source position shift, as the system 100 tends to be most sensitive to the UV spectral region spatial distribution. A DUV band pass filter at this position may provide improvement adjustment sensitivity.

In another embodiment, the direct imaging system 301 may include a position sensor. It is recognized herein that the position sensor of the direct imaging system 301 may include any position sensor known in the art. For example, the position sensor of the direct imaging system 301 may include a one-dimensional position sensor. By way of another example, the direct imaging system 301 may include a two-dimensional position sensor.

In another embodiment, as depicted in FIG. 3B, the direct imaging system 301 may include two or more cameras or two o more one-dimensional position sensors. For example, a first camera 302a may be arranged perpendicularly with respect to a second camera 302b. By way of a further example, a first positional sensor may be arranged perpendicularly with respect to a second positional. Such an arrangement may allow for the acquisition of both angular and displacement information of the illumination source 102.

It is further recognized herein that the direct imaging system 301 may include one or more optical elements (e.g., focusing lenses 306a and 306b) associated with the optical pathway between the illumination source 102 and each camera 302a,b of the direct imaging system 301.

In a further embodiment, the direct imagining system 301 may include a camera or position sensor mounted on the optics frame 204 of the system 100 such that camera or position sensor is capable of capturing imagery and/or positional data of the illumination source 102 directly.

In a further embodiment, it is contemplated herein that the direct imaging system 301 may acquire imagery or positional data at a pre-determined time. For example, a user may input a selected data acquisition frequency into the computer 206. At the pre-programmed times, the computer control system 206 may then acquire imagery or positional data using the direct imaging system 301. By way of another example, the acquisition time may be determined by the computer control system 206 based on an analyzed drift pattern associated with the illumination source 102 and the system 100.

Figure 4A:
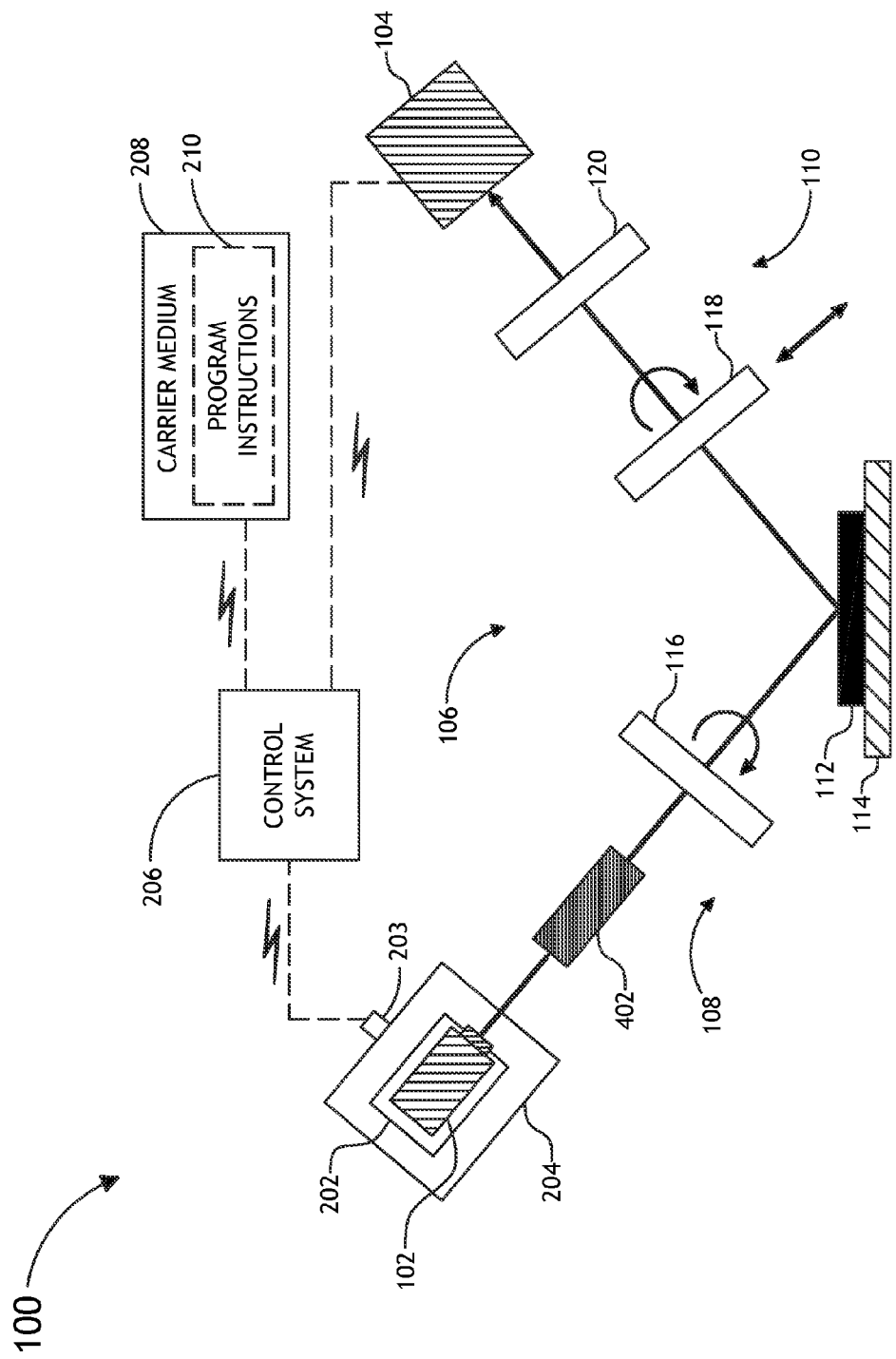
FIG. 4A illustrates a schematic view of a selectably configurable MMSE system equipped with a beam condition module, in accordance with one embodiment of the present invention.
Figure 4B:
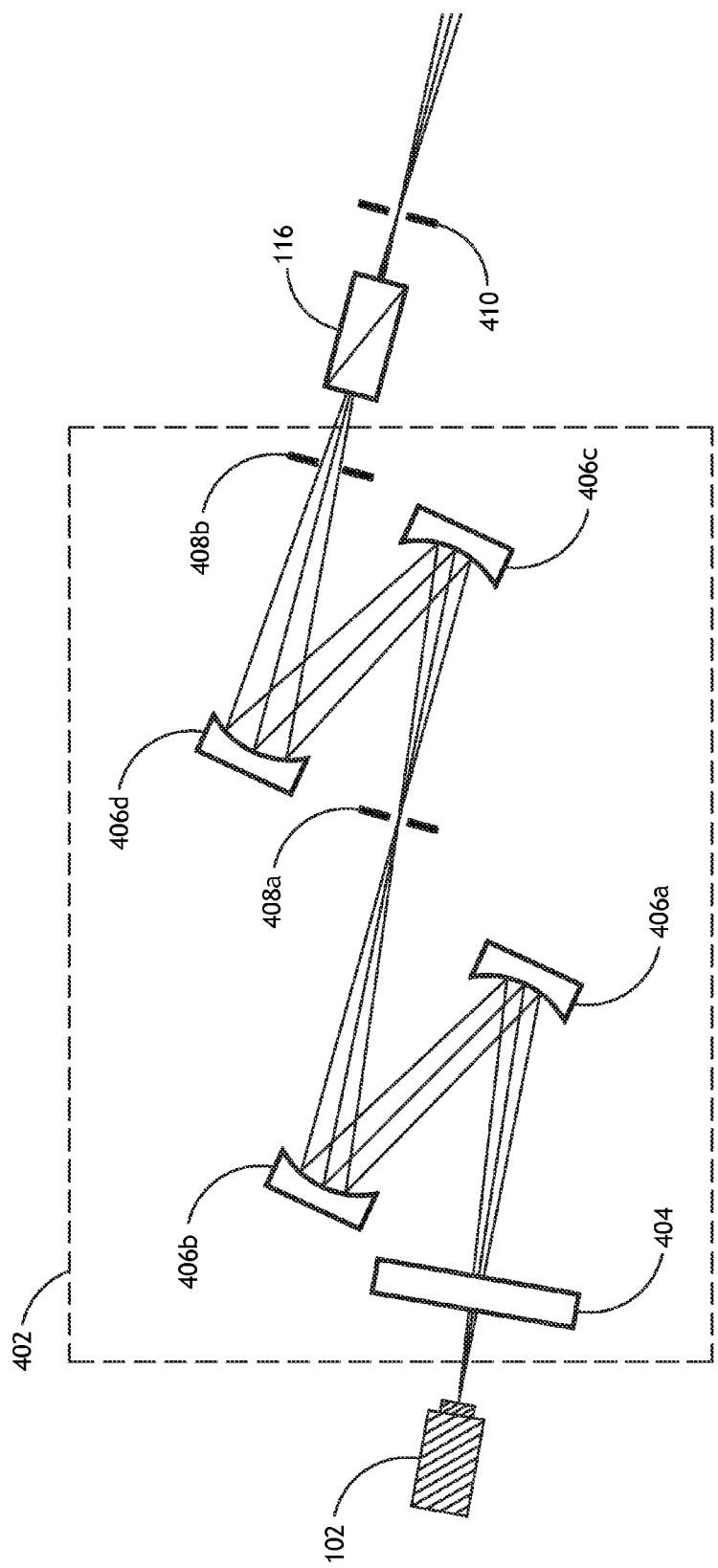
FIG. 4B illustrates a schematic view of a beam condition module suitable for implementation in the selectably configurable MMSE system, in accordance with one embodiment of the present invention.

FIGS. 4A and 4B illustrate a schematic view of the multimode SE system 100 equipped with a beam conditioning module 402, in accordance with an alternative embodiment of the present invention. The term "beam conditioning module" as used throughout the present disclosure may, in the alternative, may be referred to as a "beam conditioner" or an "illuminator."

It is recognized herein that variations in spectral intensity as function of either illumination source position or illumination wavelength may have a significant adverse effects on system performance. This behavior is compounded in settings where intermediate scramblers or homogenizers (e.g., optical fiber-wiggler or optical fiber and the like) are not arranged between the illumination source 102 and an entrance slit of a downstream optical element. Further, it is noted that illumination source non-uniformity as a function of position or wavelength combined with illumination source movement (e.g., drift) relative to the entrance slit of the polarizer 116 may degrade the performance of the system 100. For example, Poynting vector error may be introduced due to a circular trajectory, or "wobbling," of an illumination source 102 relative to a rotating polarizer (e.g., rotating polarizer in RPSE mode of system 100 or rotating polarizer in RPRC SE mode of system 100) of the illumination arm 108. This error may lead to illumination beam displacement at the illumination field stop (e.g., see 410 of FIG. 4B). In extreme settings, a plasma based broadband illumination source exhibiting a large intensity gradient may lead to the introduction of harmonics higher than a theoretical 2w into the measured signal. It is therefore desirable to introduce a direct-coupled optical system capable of limiting illumination source position drift, discussed in detail above, and illumination source variation.

In one aspect, the beam conditioning module 402 is positioned between the illumination source 102 and the entrance slit of the polarizer element 116 (e.g., rotating polarizer in RPSE or RPRC SE mode) of the illumination arm 108. In a general sense, the beam conditioning module acts to "condition" the light of the illumination path by projecting an image of the illumination source onto a portion of one or more of the optical elements (e.g., slit of polarizing element) such that the projected image has a selected level of uniformity across the projection spot.

In one embodiment, the beam conditioning module 402 of system 100 may be configured to project an image of the illumination source onto an optical element of the illumination arm such that the projected image across a selected area of a given optical element has an intensity level above a selected level. For example, the beam conditioning module 402 may be configured to project an image of the illumination source 102 onto the entrance slit of the polarizer 116 (e.g., rotating polarizer) of the illumination arm 108 such that the intensity of the image is above a sufficient level across the entire area of the entrance slit. In a general sense, it is desirable to maintain the source brightness when forming the illumination source image on the entrance slit of the polarizer 116. As such, the beam conditioning module 402 may be configured to project a source image onto the polarizer slit (or other optical element) such that projected image of the illumination source has an intensity level that is substantially similar to the illumination source intensity level.

In another embodiment, the beam conditioning module 402 of system 100 may be configured to project an image of the illumination source 102 onto an optical element of the illumination arm 108 such that the projected image across a selected area of a given optical element has an intensity gradient level below a selected level. In a general sense, it is desirable to project a uniform illumination source image onto the entrance slit of the polarizer 116 across a broad spectral range. For example, the beam conditioning module 402 may be configured to project an image of the illumination source 102 onto the entrance slit of the polarizer 116 (e.g., rotating polarizer) of the illumination arm 108 such that the intensity gradient of the image is below a selected level across the entire area of the entrance slit across a broad spectral range (e.g., significant portion of spectral range of illumination source).

In one embodiment, the beam conditioning module 402 may include one or more mirrors 406a . . . 406d configured to project an image of the illumination source 102 onto an optical element of the illumination arm 108 such that image has an intensity level above a selected level, while maintaining intensity uniformity (i.e., intensity gradient is below an adequate level). In one aspect, the set of mirrors 406a . . . 406d of the beam conditioning module 402 may include one or more spherical mirrors. The spherical mirrors of the beam conditioning module 402 may be configured to minimize low spatial frequency scattering. In another aspect, the set of mirrors 406a . . . 406d of the beam conditioning module 402 may include one or more non-spherical mirrors. It is recognized herein that one or more non-spherical mirrors may be implemented within the beam conditioning module 402 in order to limit design complexity of the beam condition module 402.

In another embodiment, one or more internal pupil and/or field stops 408a, 408b may be included within in the optical pathway of the beam conditioning module 402 in order to reject scattering and stray light from reaching the illumination field stop 410.

The mirrors 406a . . . 406d of the beam module 402 may be configured to provide magnification greater than unity. In this regard, the mirrors 406a . . . 406d may be utilized to magnify the image of the illumination source 102 such that only the "sweet spot" (i.e., portion of illumination distribution having highest intensity level) passes through the illumination field stop of the illumination image of the illumination source 102 pass through the illumination field stop 410.

It is recognized herein that several factors may be considered when determining the degree of magnification of the beam condition module 402. For example, the chosen degree of magnification may depend on the size of the illumination beam sought to be implemented, the illumination uniformity required for the given application (i.e., metrology system specifications), and the polarizer 116 slit size, among other factors.

Further, as shown in FIG. 4B, the projection of the sweet spot onto the polarizer slit may be accomplished with manageable spectral angular distribution by projecting the illumination source 102 image at near normal incidence (e.g., via mirrors 406a . . . 406d) to downstream optical elements (e.g., polarizer 116) in a given oblique incidence metrology tool.

In another aspect, the angle of incident of illumination and the relative orientation of the various optical components (e.g., mirrors 406a . . . 406d) may be selected and configured to provide an illumination beam with residual polarization below a selected level. In this regard, the beam conditioning module 402 may be configured to minimize residual polarization via implementation of a low angle of incidence optical design and selected relative orientations of the various optical components such that birefringence induced by the optical coatings of the various optical components of the beam conditioning module 402 is below a selected level (e.g., birefringence is minimized). Those skilled in the art will recognize that coating induced birefringence is dependent upon both the angle of incidence of illumination relative to a coating surface and the thickness of the coating thickness.

Figure 5:
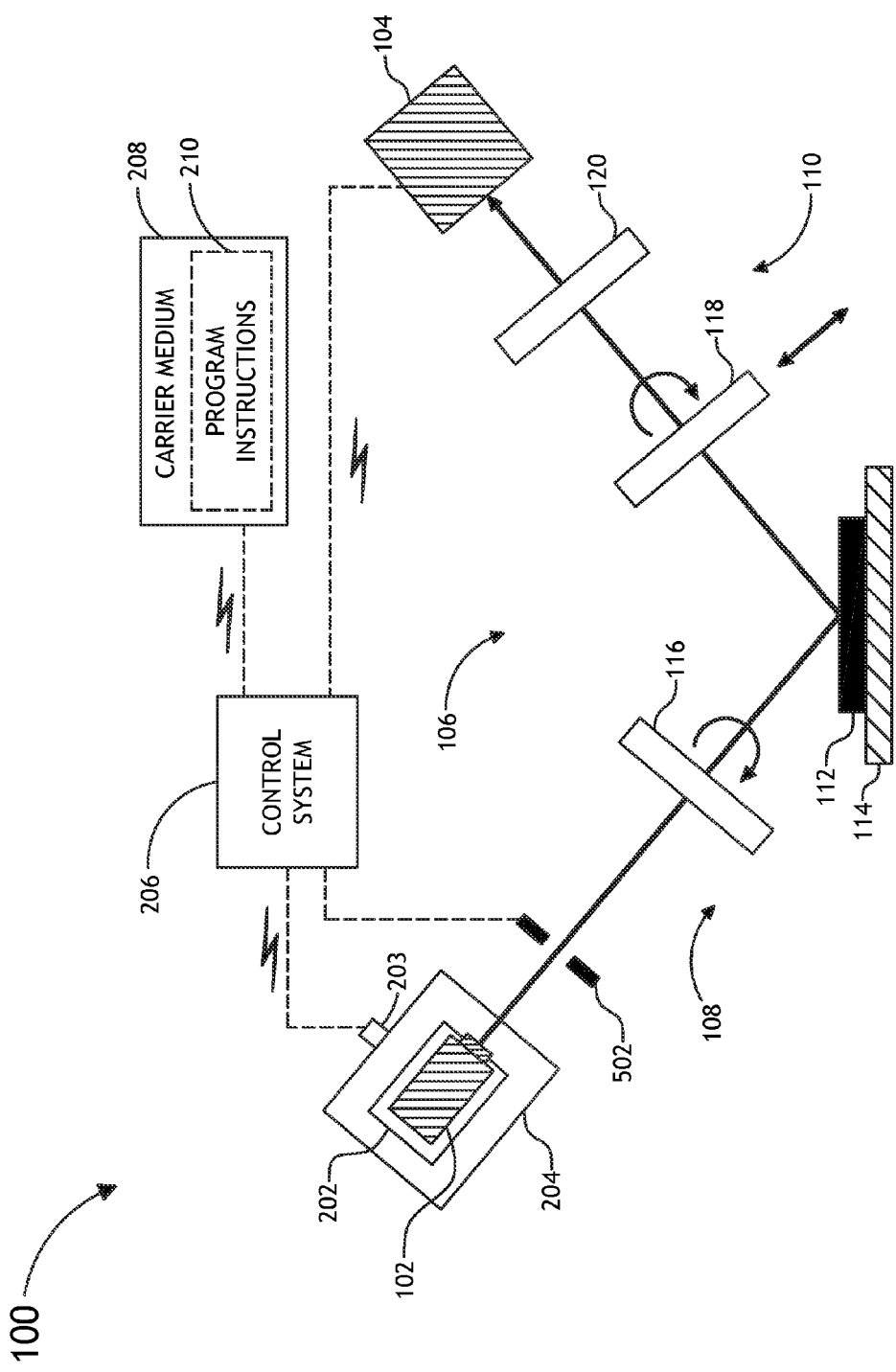
FIG. 5 illustrates a schematic view of a selectably configurable MMSE system equipped with an adjustable polarization slit, in accordance with one embodiment of the present invention.

FIG. 5 illustrates a schematic view of the multimode SE system 100 equipped with an adjustable polarization slit 502, in accordance with an alternative embodiment of the present invention. In one aspect, the adjustable polarization slit 502 is positioned along the illumination arm 108 of the optical system 106 between the illumination source 102 and the polarizer 116. The adjustable polarization slit 502 may be utilized by the system 100 in order to adjust the size of the polarization slit 502 to a size providing adequate illumination beam uniformity. In this sense, the adjustable polarization slit 502 may be utilized to isolate the sweet spot of the illumination beam from the less intense and less uniform portions of the illumination beam. It is recognized herein that the amount of adjustment required may depend on several factors, such as, but not limited to, required illumination beam brightness and required intensity uniformity of the system 100.

The adjustable polarization slit 502 may include any adjustable polarization slit 502 known in the art. For example, the adjustable polarization slit 502 may include an adjustable polarization slit capable of adjustment in one dimension. For instance, the adjustable polarization slit 502 may include an adjustable polarization slit capable of adjusting the slit height or the slit width. By way of another example, the adjustable polarization slit 502 may include an adjustable polarization slit capable of adjustment in two dimensions. For instance, the adjustable polarization slit 502 may include an adjustable polarization slit capable of adjusting the slit height and the slit width or a square or rectangular slit. It is contemplated herein that a four-knife-edge-based adjustable slit is suitable for adjusting the slit size in two dimensions. In other instances, the slit may include any geometric shape known in the art. For example, the slit may include a circular slit, an oval slit, and the like.

In one embodiment, the adjustable polarization slit 502 may include an adjustable polarization slit 502 driven by one or motorized micrometers. It is recognized herein that any motorized micrometer known in the art is suitable for implementation in the present invention. In another embodiment, the adjustable polarization slit 502 may include an adjustable polarization slit 502 driven by one or more piezoelectric actuators. It is recognized herein that any piezoelectric actuator known in the art is suitable for implementation in the present invention.

In one aspect, the adjustable polarization slit 502 may be communicatively coupled to the computer control system 206. In this sense, the adjustable polarization slit 502 may be configured to receive instruction signals from the computer control system 206. In one embodiment, the computer control system 206 may transmit instructions to the adjustable polarization slit 502 based on results from a source position diagnostic algorithm 212, as discussed in greater detail above. In this manner, the source position diagnostic algorithm 212 may be configured to incorporate the ability to adjust the polarization slit height or width when determining the position adjustment parameters for the multi-axis actuation stage 202. In this sense, the computer control system 206 may supply adjustment parameters to either the multi-axis actuation stage 202 or the adjustable polarization slit 502 or both based on the source position diagnostic algorithm 212 executed by the computer control system 206.

In another embodiment, the computer control system 206 may transmit instructions to the adjustable polarization slit 502 based on results from a source position imaging algorithm 305, as discussed in greater detail above. In this manner, the source position imaging algorithm 305 may be configured to incorporate the ability to adjust the polarization slit height or width when determining the position adjustment parameters for the multi-axis actuation stage 202. In this sense, the computer control system 206 may supply adjustment parameters to either the multi-axis actuation stage 202 or the adjustable polarization slit 502 or both based on the position imaging algorithm executed by the computer control system 206.

In another embodiment, the computer control system 206 may transmit instruction to the adjustable polarization slit 502 based on user input. In this manner, a user may enter instructions into the computer control system 206 via one or more user interfaces (not shown). Then, the computer control system 206 may transmit corresponding instruction signals to the adjustable polarization slit 502. In a further embodiment, user input may be combined with the results of the source position diagnostic algorithm 305 or the source position imaging algorithm 305 by the computer control system 206 in order to achieve improved illumination characteristics of the system 100.

It is further contemplated herein that the adjustable polarization slit 502 may be implemented in conjunction with the beam condition module 402, providing for even greater control of illumination source brightness and intensity uniformity. In this sense, although not shown, the beam conditioning module 402 may be positioned between the illumination source 102 and the entrance of the adjustable polarization slit 502.

Figure 6:
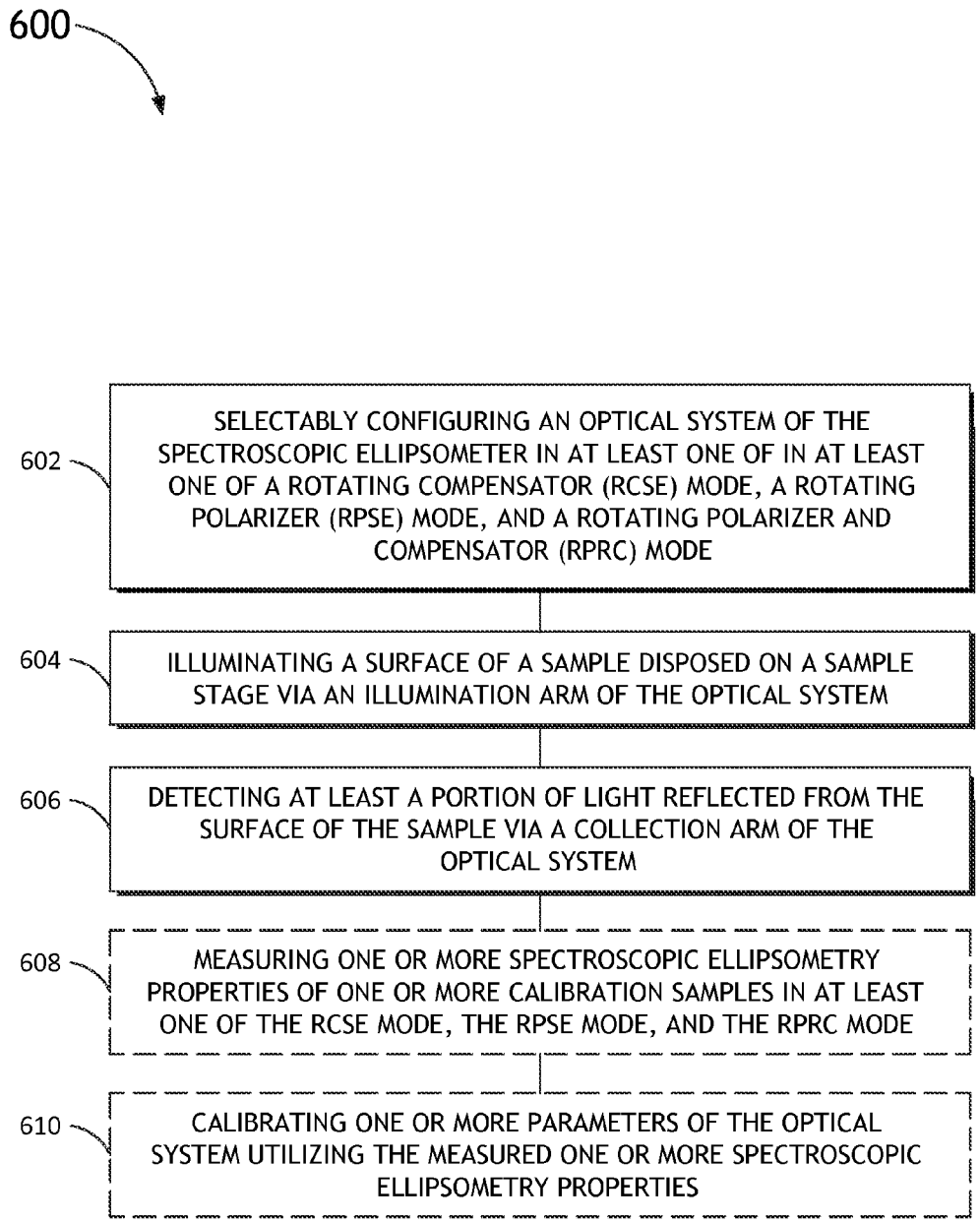
FIG. 6 is a flow diagram illustrating a method for performing multiple mode spectroscopic ellipsometry, in accordance with one embodiment of the present invention.

FIG. 6 illustrates a process flow 600 suitable for implementation by the system 100 of the present invention. In step 602, an optical system 106 of the spectroscopic ellipsometer may be selectably configured in at least one of in at least one of a rotating compensator (RCSE) mode, a rotating polarizer (RPSE) mode, and a rotating polarizer and compensator (RPRC) mode. In step 604, upon being configured in one of the above modes, a surface of a sample disposed on a sample stage may be illuminated by an illumination source 102 via an illumination arm 108 of the optical system 106. In step 606, at least a portion of light reflected from the surface of the sample 112 via a collection arm 110 of the optical system 106 may be detected utilizing a detector 104. In a further step of process flow 600, one or more spectroscopic ellipsometry properties of one or more calibration samples may be measured in at least one of the RCSE mode, the RPSE mode, and the RPRC mode in at least one of the RCSE mode, the RPSE mode, and the RPRC mode. In a further step of process flow 600, the optical system 106 may be calibrated utilizing the measured one or more spectroscopic ellipsometry properties.

Figure 7:
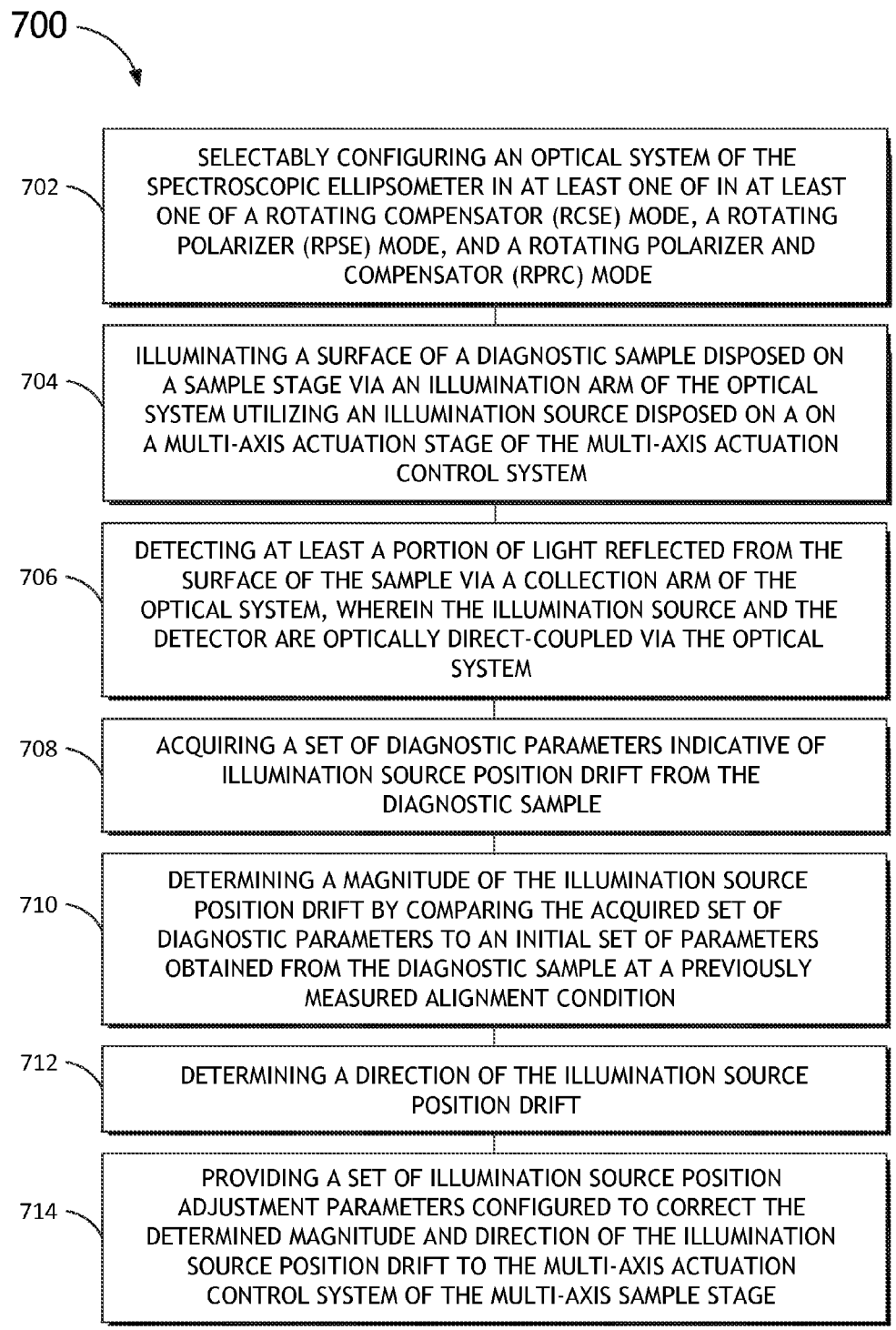
FIG. 7 is a flow diagram illustrating a method for performing multiple mode spectroscopic ellipsometry, in accordance with an alternative embodiment of the present invention.

FIG. 7 illustrates an alternative process flow 700 suitable for implementation by the system 100 of the present invention. In step 702, an optical system 106 of the spectroscopic ellipsometer may be selectably configured in at least one of in at least one of a rotating compensator (RCSE) mode, a rotating polarizer (RPSE) mode, and a rotating polarizer and compensator (RPRC) mode. In step 704, a surface of a diagnostic sample disposed on a sample stage may be illuminated via an illumination arm of the optical system utilizing an illumination source 102 disposed on a on a multi-axis actuation stage 202 of a multi-axis actuation control system 204. In step 706, at least a portion of light reflected from the surface of the diagnostic sample may be detected via a collection arm of the optical system, wherein the illumination source and the detector are optically direct-coupled via the optical system. In step 708, a set of diagnostic parameters indicative of illumination source position drift may be acquired from the diagnostic sample. In step 710, a magnitude of the illumination source position drift may be determined by comparing the acquired set of diagnostic parameters to an initial set of parameters obtained from the diagnostic sample at a previously measured alignment condition. In step 712, a direction of the illumination source position drift may be determined. In step 714, a set of illumination source position adjustment parameters configured to correct the determined magnitude and direction of the illumination source position drift may be provided to the multi-axis actuation control system 204 of the multi-axis sample stage 202. In a further step of process flow 700, a position of the illumination source may be adjusted utilizing the provided set of illumination source position adjustment parameters utilizing the multi-axis sample stage 202 of the multi-axis actuation control system 204.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. An apparatus suitable for multiple mode spectroscopic ellipsometry, comprising:
   an illumination source configured to illuminate a surface of a sample disposed on a sample stage;
   a detector configured to detect at least a portion of light reflected from the surface of the sample;
   a selectably configurable optical system including an illumination arm and a collection arm, the illumination source and the detector being optically coupled by the optical system, the optical system further comprising:
      a rotatable polarizing element disposed in the illumination arm of the optical system, the rotatable polarizing element being rotatable about an optical axis of the illumination arm;
      an analyzing element disposed in the collection arm of the optical system and arranged at a selected analyzer angle; and
      a rotatable-translatable compensator element disposed in the collection arm of the optical system, the rotatable-translatable compensator element being rotatable about an optical axis of the collection arm, the rotatable-translatable compensator element being linearly translatable along a direction perpendicular to the optical axis of the collection arm; and
   a control system communicatively coupled to the rotatable polarizing element and the rotatable-translatable compensator element, wherein the control system is configured to selectably configure the optical system in at least one of a rotating compensator (RCSE) mode, a rotating polarizer (RPSE) mode, and a rotating polarizer and compensator (RPRC) mode by controlling an operation state of at least one of the rotatable polarizing element and the rotatable-translatable compensator element.

2. The apparatus of claim 1, wherein the illumination source comprises:
   at least one broad band illumination source.

3. The apparatus of claim 1, wherein the rotatable polarizing element comprises:
   a polarizer disposed on a rotatable unit driven by a rotating motor and configured to rotate the polarizer.

4. The apparatus of claim 1, wherein the rotatable-translatable compensator element comprises:
   a compensator disposed on a rotatable unit driven by a rotating motor and configured to rotate the compensator, wherein the rotatable unit is disposed on a linear translation stage configured to linearly translate the compensator and rotatable unit.

5. The apparatus of claim 1, wherein the rotating compensator RPSE mode comprises:
   a polarizer of the rotatable polarizer element positioned along the optical axis of the illumination arm, wherein the polarizer is rotating at a selected polarizer angular frequency; and
   a compensator of the rotatable-translatable compensator element displaced from the optical axis of the collection arm.

6. The apparatus of claim 1, wherein the rotating compensator RCSE mode comprises:
   a polarizer of the rotatable polarizer element positioned along an optical axis of the illumination arm, wherein the polarizer is non-rotating; and
   a compensator of the rotatable-translatable compensator element positioned along an optical axis of the collection arm, wherein the compensator is rotating at a selected compensator angular frequency.

7. The apparatus of claim 1, wherein the rotating compensator RPRC SE mode comprises:
   a polarizer of the rotatable polarizer element positioned along an optical axis of the illumination arm, wherein the polarizer is rotating at a selected polarizer angular frequency; and
   a compensator of the rotatable-translatable compensator element positioned along an optical axis of the collection arm, wherein the compensator is rotating at a selected compensator angular frequency.

8. The apparatus of claim 1, wherein the control system is configured to transition the selectably configurable optical system from the RCSE configuration to at least one the RPSE configuration and the RPRC SE configuration.

9. The apparatus of claim 1, wherein the control system is configured to transition the selectably configurable optical system from the RPSE configuration to at least one the RCSE configuration and the RPRC SE configuration.

10. The apparatus of claim 1, wherein the control system is configured to transition the selectably configurable optical system from the RPRC configuration to at least one the RPSE configuration and the RCSE configuration.

11. The apparatus of claim 1, wherein the selectably configurable optical system comprises:
    a selectably configurable reflective-based optical system.

12. The apparatus of claim 1, wherein the selectably configurable optical system comprises:
    a selectably configurable refractive-based optical system.

13. The apparatus of claim 1, wherein the illumination source and the detector are optically via one or more optical fibers.

14. The apparatus of claim 1, wherein the illumination source and the detector are optically direct-coupled.

15. The apparatus of claim 14, further comprising:
    a multi-axis actuation control system, wherein the illumination source is disposed on a multi-axis actuation stage of the multi-axis actuation control system;
    an additional control system communicatively coupled to the multi-axis actuation control system and the detector, wherein the control system is configured to:
       acquire a set of diagnostic parameters from a diagnostic sample disposed on the sample stage, wherein the set of diagnostic parameters are indicative of position drift of the illumination source as measured relative to one or more components of the optical system;

determine a magnitude of illumination source position drift by comparing the acquired set of diagnostic parameters to an initial set of parameters obtained from the diagnostic sample at a previously measured alignment condition;

determine a direction of illumination source position drift; and provide a set of illumination source position adjustment parameters configured to correct the determined magnitude and direction of the illumination source position drift to the multi-axis actuation control system.

16. The apparatus of claim 15, wherein the multi-axis actuation stage comprises at least one of a multi-axis translation stage or a multi-axis rotational stage.

17. The apparatus of claim 15, wherein the additional control system is configured to determine a direction of illumination source position drift by transmitting a set of command signals to the multi-axis actuation control system in order to translate the illumination source by the determined magnitude along a first direction and a second direction orthogonal to the first direction.

18. The apparatus of claim 17, further comprising:

a conditioning module positioned between the illumination source and the rotatable polarizing element of the illumination arm, wherein the conditioning module is configured to project an image of the illumination source having a selected level of uniformity onto a portion of one or more optical elements of the illumination arm.

19. The apparatus of claim 18, wherein the condition module comprises:

a conditioning module configured to project an image of the illumination source onto a slit of the rotatable polarizing element of the illumination arm.

20. The apparatus of claim 17, further comprising:

an adjustable optical slit positioned between the illumination source and the rotatable polarizing element of the illumination arm, the adjustable optical slit being communicatively coupled to the additional control system, wherein the adjustable slit is configured to adjust in response to instructions received from the additional control system.

21. The apparatus of claim 15, wherein the set of diagnostic parameters are acquired by the additional control system via a diagnostic sequence, wherein the diagnostic sequence is configured to decouple illumination source intensity decay and sample property changes from the illumination source position drift.

22. The apparatus of claim 15, wherein the initial set of parameters are acquired by the additional control utilizing imagery data of the diagnostic sample collected at a selected alignment condition.

23. The apparatus of claim 22, wherein the selected alignment condition comprises a substantially optimum alignment condition.

24. The apparatus of claim 14, further comprising:

a multi-axis actuation control system, wherein the illumination source is disposed on a multi-axis actuation stage of the multi-axis actuation control system;

a direct imaging system configured to measure at least one of a position of the illumination source or a spatial distribution of light intensity of the illumination emitted by the illumination source;

an additional control system communicatively coupled to the multi-axis actuation control system, the direct imaging system, and the detector, wherein the additional control system is configured to:

determine illumination source position drift by comparing the one or more acquired images of the illumination source to one or more images of an initial set of images of the illumination source obtained at a previously measured alignment condition; and provide a set of illumination source position adjustment parameters configured to correct the determined illumination source drift to the multi-axis actuation control system.

25. The apparatus of claim 24, wherein the direct imaging system includes at least one of a camera, a one-dimensional position sensor, or a two-dimensional position sensor.

26. An apparatus suitable for calibrated multiple mode spectroscopic ellipsometry suitable for calibration of one or more ellipsometric parameters, comprising:

an illumination source configured to illuminate a surface of a calibration sample disposed on a sample stage;

a detector configured to collect at least a portion of light reflected from the surface of the calibration sample;

a selectably configurable optical system including an illumination arm and a collection arm, the illumination source and the detector being optically coupled by the optical system, the optical system further comprising:

a rotatable polarizing element disposed in the illumination arm of the optical system, the rotatable polarizing element being rotatable about an optical axis of the illumination arm;

an analyzing element disposed in the collection arm of the optical system and arranged at a selected analyzer angle; and a rotatable-translatable compensator element disposed in the collection arm of the optical system, the rotatable-translatable compensator element being rotatable about an optical axis of the collection arm, the rotatable-translatable compensator element being linearly translatable along a direction perpendicular to the optical axis of the collection arm; and a control system communicatively coupled to the rotatable polarizing element and the rotatable and translatable compensator element, wherein the control system is configured to:

configure the optical system in at least one of a rotating compensator (RCSE) mode, a rotating polarizer (RPSE) mode, and a rotating polarizer and compensator (RPRC) mode;

measuring one or more spectroscopic ellipsometry properties of one or more calibration samples in at least one of the RCSE mode, the RPSE mode, and the RPRC mode; and calibrating one or more parameters of the optical system utilizing the measured one or more spectroscopic ellipsometry properties.

27. A method for performing multiple mode spectroscopic ellipsometry, comprising:

selectably configuring an optical system of the spectroscopic ellipsometer in at least one of a rotating compensator (RCSE) mode, a rotating polarizer (RPSE) mode, and a rotating polarizer and compensator (RPRC) mode with a control system communicatively coupled to a rotatable polarizing element and a rotatable-translatable compensator element of the optical system;

illuminating a surface of a sample disposed on a sample stage via an illumination arm of the optical system; and detecting at least a portion of light reflected from the surface of the sample via a collection arm of the optical system;

acquiring one or more images of the illumination source in order to measure at least one of a position of the illumination source or a spatial distribution of light intensity of the illumination emitted by the illumination source;

determining illumination source drift by comparing the one or more acquired images of the illumination source to an initial set of images of the illumination source obtained at a previously measured alignment condition; and providing a set of illumination source position adjustment parameters configured to correct the determined illumination source drift to a multi-axis actuation control system configured to actuate the illumination source.

28. The method of claim 27, further comprising:

measuring one or more spectroscopic ellipsometry properties of one or more calibration samples in at least one of the RCSE mode, the RPSE mode, and the RPRC mode; and calibrating the optical system utilizing the measured one or more spectroscopic ellipsometry properties.

29. A method for performing multiple mode spectroscopic ellipsometry, comprising:

selectably configuring an optical system of the spectroscopic ellipsometer in at least one of in at least one of a rotating compensator (RCSE) mode, a rotating polarizer (RPSE) mode, and a rotating polarizer and compensator (RPRC) mode;

illuminating a surface of a diagnostic sample disposed on a sample stage via an illumination arm of the optical system utilizing an illumination source disposed on a multi-axis actuation stage of a multi-axis actuation control system;

detecting at least a portion of light reflected from the surface of the diagnostic sample via a collection arm of the optical system, wherein the illumination source and the detector are optically direct-coupled via the optical system;

acquiring a set of diagnostic parameters indicative of illumination source position drift from the diagnostic sample;

determining a magnitude of the illumination source position drift by comparing the acquired set of diagnostic parameters to an initial set of parameters obtained from the diagnostic sample at a previously measured alignment condition;

determining a direction of the illumination source position drift; and providing a set of illumination source position adjustment parameters configured to correct the determined magnitude and direction of the illumination source position drift to the multi-axis actuation control system of the multi-axis sample stage.

30. The method of claim 29, further comprising:

adjusting a position of the illumination source utilizing the provided set of illumination source position adjustment parameters utilizing the multi-axis sample stage of the multi-axis control system.

* * * * *